United States Patent
Preuss et al.

(10) Patent No.: US 11,216,784 B2
(45) Date of Patent: Jan. 4, 2022

(54) SYSTEMS AND METHODS FOR AUTOMATING VALIDATION AND QUANTIFICATION OF INTERVIEW QUESTION RESPONSES

(71) Applicant: Cut-E Assessment Global Holdings Limited, Loughrea (IE)

(72) Inventors: Achim Preuss, Hamburg (DE);
Richard Justenhoven, Hamburg (DE);
Mario Martella, Hamburg (DE);
Andrey Matveev, Hamburg (DE);
Nicholas Martin, Austin, TX (US)

(73) Assignee: Cut-E Assessment Global Holdings Limited, Loughrea (IE)

( * ) Notice: Subject to any disclaimer, the term of this patent is extended or adjusted under 35 U.S.C. 154(b) by 0 days.

(21) Appl. No.: 17/160,165

(22) Filed: Jan. 27, 2021

(65) Prior Publication Data
US 2021/0233031 A1 Jul. 29, 2021

Related U.S. Application Data

(60) Provisional application No. 62/967,451, filed on Jan. 29, 2020.

(51) Int. Cl.
*G06K 9/00* (2006.01)
*G06Q 10/10* (2012.01)
(Continued)

(52) U.S. Cl.
CPC ......... *G06Q 10/1053* (2013.01); *A61B 5/164* (2013.01); *A61B 5/165* (2013.01);
(Continued)

(58) Field of Classification Search
CPC ........... G06K 9/00221; G06K 9/00302; G06K 9/00308; G06K 9/00315; G06K 9/00335;
(Continued)

(56) References Cited

U.S. PATENT DOCUMENTS 8,856,000 B1 10/2014 Larsen et al.
9,009,045 B1 4/2015 Larsen et al.
(Continued)

FOREIGN PATENT DOCUMENTS

CN 109146296 1/2019
WO WO2015198317 12/2015
(Continued)

OTHER PUBLICATIONS

"Reliability coefficient," American Psychological Association, APA Dictionary of Psychology. Retrieved Jan. 27, 2021, from https://dictionary.apa.org/reliability-coefficient.
(Continued)

*Primary Examiner* — Eric Rush
(74) *Attorney, Agent, or Firm* — Gardella Grace P.A.

(57) ABSTRACT

In an illustrative embodiment, systems and methods for automating candidate video assessments include receiving a submission from a candidate for an available position including baseline response video segments and question response video segments. The system can determine, from detected nonverbal features within the baseline response video segments, nonverbal baseline scores. For each of the interview questions, candidate response attributes can be detected including a response direction, a response speed, and nonverbal features. A nonverbal reaction score is calculated from the detected nonverbal features and the baseline scores. A response score can be calculated from the response direction and response speed, and a trustworthiness score is determined based on a correspondence between the response score and the nonverbal reaction score. A next interview question can be determined in real-time from a benchmarked version of the response score. Overall scores reflecting candidate trustworthiness can be presented within a user interface screen.

18 Claims, 7 Drawing Sheets

(51) Int. Cl.
  *G09B 7/02* (2006.01)
  *G10L 15/18* (2013.01)
  *A61B 5/16* (2006.01)
  *G10L 25/63* (2013.01)

(52) U.S. Cl.
  CPC .......... *A61B 5/167* (2013.01); *G06K 9/00221* (2013.01); *G06K 9/00302* (2013.01); *G06K 9/00315* (2013.01); *G06K 9/00335* (2013.01); *G09B 7/02* (2013.01); *G10L 15/1807* (2013.01); *G10L 25/63* (2013.01)

(58) Field of Classification Search
  CPC .. G06Q 10/1053; G09B 7/02; G10L 15/1807; G10L 25/63; A61B 5/16; A61B 5/163; A61B 5/164; A61B 5/165; A61B 5/167; G06F 2203/011
  USPC ........ 382/100, 115–118, 181, 224, 226–229, 382/325; 705/321
  See application file for complete search history.

(56) References Cited

U.S. PATENT DOCUMENTS

| | | | |
|---|---|---|---|
| 9,846,844 | B2 | 12/2017 | Hecht et al. |
| 10,104,233 | B2 | 10/2018 | Conway et al. |
| 10,176,365 | B1 | 1/2019 | Ramanarayanan et al. |
| 10,242,345 | B2* | 3/2019 | Taylor ................ G06Q 10/1053 |
| 10,318,926 | B2 | 6/2019 | Champaneria |
| 10,318,927 | B2 | 6/2019 | Champaneria |
| 10,366,160 | B2 | 7/2019 | Castelli et al. |
| 10,796,217 | B2* | 10/2020 | Wu ..................... G06Q 10/1053 |
| 2004/0093263 | A1 | 5/2004 | Doraisamy et al. |
| 2005/0283378 | A1 | 12/2005 | Iserson |
| 2007/0088601 | A1 | 4/2007 | Money et al. |
| 2008/0270467 | A1 | 10/2008 | Clarke |
| 2011/0088081 | A1 | 4/2011 | Folkesson et al. |
| 2012/0221477 | A1 | 8/2012 | Pande |
| 2012/0262296 | A1* | 10/2012 | Bezar ...................... G10L 25/63 340/573.1 |
| 2013/0226578 | A1 | 8/2013 | Bolton et al. |
| 2013/0266925 | A1* | 10/2013 | Nunamaker, Jr. ....... G06N 20/00 434/362 |
| 2013/0290210 | A1 | 10/2013 | Cline et al. |
| 2014/0191939 | A1* | 7/2014 | Penn ........................ G06F 3/015 345/156 |
| 2014/0356822 | A1* | 12/2014 | Hoque ...................... G09B 7/00 434/185 |
| 2015/0046357 | A1* | 2/2015 | Danson .............. G06Q 10/1053 705/321 |
| 2015/0206103 | A1 | 7/2015 | Larsen et al. |
| 2015/0269529 | A1 | 9/2015 | Kyllonen et al. |
| 2016/0034851 | A1 | 2/2016 | Xiao et al. |
| 2017/0116870 | A1* | 4/2017 | Brem ........................ G09B 7/02 |
| 2017/0213190 | A1* | 7/2017 | Hazan ................ G06Q 10/1053 |
| 2017/0262949 | A1 | 9/2017 | Jay |
| 2018/0025303 | A1 | 1/2018 | Janz |
| 2019/0096425 | A1 | 3/2019 | Akkiraju et al. |
| 2020/0168231 | A1* | 5/2020 | Alagianambi ..... G06K 9/00302 |
| 2020/0311682 | A1* | 10/2020 | Olshansky ......... G06K 9/00315 |
| 2020/0387850 | A1 | 12/2020 | Kramer et al. |
| 2021/0192221 | A1* | 6/2021 | Iyer .................... G06K 9/00744 |
| 2021/0233030 | A1 | 7/2021 | Preuss et al. |

FOREIGN PATENT DOCUMENTS

| | | |
|---|---|---|
| WO | 2021151990 | 8/2021 |
| WO | 2021151993 | 8/2021 |

OTHER PUBLICATIONS

Argamon et al., "Lexical predictors of personality type," Proceedings of Joint Annual Meeting of the Interface and the Classification Society of North America, 2005, 16 pages.

Blackman, "Personality Judgment and the Utility of the Unstructured Employment Interview," Basic and Applied Social Psychology, 2002, 24(3), pp. 241-250.

Blacksmith et al., "Technology in the employment interview: A meta-analysis and future research agenda," Personnel Assessment and Decisions, 2016, 2(1), pp. 12-20.

Brenner et al., "Asynchronous video interviewing as a new technology in personnel selection: The applicant's point of view," Frontiers in Psychology, 2016, vol. 7, Article 863, 11 pages.

Chen et al., "Automated scoring of interview videos using Doc2Vec multimodal feature extraction paradigm" Proceedings of the 18th ACM International Conference on Multimodal Interaction, 2016, pp. 161-168.

Clark et al., "Electra: Pre-training text encoders as discriminators rather than generators," 2020, arXiv preprint arXiv:2003.10555, 18 pages.

Cohen, "The effect size index: d," Statistical power analysis for the behavioral sciences, Second Edition, pp. 20-27, 1988.

Cohen, "A Power Primer," Psychological Bulletin, 1992, 112(1), pp. 155-159.

Conway et al., "A meta-analysis of interrater and internal consistency reliability of selection interviews," Journal of applied psychology, 1995, 80(5), pp. 565-579.

Cronbach et al., "Construct validity in psychological tests," Psychological Bulletin, 1955, 52, 281-302.

D'Urso et al., "Examining the scope of channel expansion: A test of channel expansion theory with new and traditional communication media," Management Communication Quarterly, 2008, 21(4), pp. 486-507.

Davenport et al., "Artificial Intelligence or the Real World," Harvard Business Review, 2018, from: https://hbr.org/2018/01/artificial-intelligence-for-the-real-world.

Degroot et al., "Evidence of predictive and incremental validity of personality factors, vocal attractiveness and the situational interview" International Journal of Selection and Assessment, 2007, 15(1), pp. 30-39.

Devlin et al., "Bert: Pre-training of deep bidirectional transformers for language understanding," 2019, arXiv preprint arXiv:1810.04805.

Eisinga et al., "The reliability of a two-item scale: Pearson, Cronbach or Spearman-Brown?" International Journal of Public Health, 2013, 58, pp. 637-642. doi: 10.1007 / s00038-012-0416-3.

Fast et al., "Personality as manifest in word use: correlations with self-report, acquaintance report, and behavior," Journal of Personality and Social Psychology, 2008, 94(2), pp. 334-346.

Gliozzo et al., "Building Cognitive Applications with IBM Watson Services: Volume 1—Getting started," IBM Redbooks, 2017, 131 pages.

Goodfellow et al., "Generative adversarial nets," Advances in Neural Information Processing Systems, 2014, arXiv:1406.2661.

Gorman et al., "An investigation into the validity of asynchronous web-based video employment-interview ratings," Consulting Psychology Journal: Practice and Research, 2018, 70(2), pp. 129-146.

Huffcutt et al., "Racial group differences in employment interview evaluations," Journal of Applied Psychology, 1998, 83(2), pp. 179-189.

Huffcutt et al., "Understanding applicant behavior in employment interviews: A theoretical model of interviewee performance," Human Resource Management Review, 2011, 21, pp. 353-367.

IBM (2017). Reaching new records in speech recognition. Retrieved from: https://www.ibm.com/blogs/watson/2017/03/reaching-new-records-in-speech-recognition/, 2017.

IBM (2020a). Best practices for classifiers. Retrieved from: https://cloud.ibm.com/docs/services/natural-language-classifier?topic=natural-language-classifier-best-practices-overview, 2020.

IBM (2020b). Text-to-Speech Release Notes. Retrieved from: https://cloud.ibm.com/docs/text-to-speech?topic=text-to-speech-release-notes, 2020.

IBM (2020c). Speech-to-Text Documentation. Retrieved from: https://cloud.ibm.com/docs/speech-to-text, 2020.

(56) References Cited

OTHER PUBLICATIONS

Jongman et al., "Vocabulary size influences spontaneous speech in native language users: Validating the use of automatic speech recognition in individual differences research," Language and Speech, 2020 pp. 1-17.

Kubis et al., "Open Challenge for Correcting Errors of Speech Recognition Systems," 2020, arXiv preprint arXiv:2001.03041.

Landy, "Stamp collecting versus science: Validation as hypothesis testing," American Psychologist, 1986, 41(11), pp. 1183-1192.

Latif et al., "Deep Representation Learning in Speech Processing: Challenges, Recent Advances, and Future Trends," arXiv preprint arXiv:2001.00378, 2020.

Lochner et al., "Digitales Recruiting," Group, Interaction, Organization, Journal of Applied Organizational Psychology (GIO), 2018, 49(3), pp. 193-202.

Macan, "The employment interview: A review of current studies and directions for future research," Human Resource Management Review, 2009, 19(3), pp. 203-218.

Mejia et al., "Implementation and normalization process of asynchronous video interviewing practices in the hospitality industry," International Journal of Contemporary Hospitality Management, 2018, 30(2), pp. 685-701.

International Search Report and Written Opinion issued in International Application No. PCT/EP2021/051951 dated Apr. 1, 2021.

Hemamou, L. et al., "Slices of Attention in Asynchronous Video Job Interviews." 2019 8th International Conference on Affective Computing and Intelligent Interaction (ACII). IEEE, 2019. (Year: 2019).

Suen, H. et al., "TensorFlow-based automatic personality recognition used in asynchronous video interviews." IEEE Access 7 (2019): 61018-61023. (Year: 2019).

Notice of Allowance dated Apr. 2, 2021 for U.S. Appl. No. 17/160,131.

Bias, AI Ethics, and the HireVue Approach, HireVue, Retrieved on Oct. 16, 2019 at: https://www.hirevue.com/why-hirevue/ethical-ai, 3 pages.

International Search Report and Written Opinion issued in International Application No. PCT/EP2021/051946 dated May 3, 2021.

\* cited by examiner

SYSTEMS AND METHODS FOR AUTOMATING VALIDATION AND QUANTIFICATION OF INTERVIEW QUESTION RESPONSES

RELATED APPLICATIONS

This application claims priority to U.S. Provisional Patent Application Ser. No. 62/967,451, entitled "Systems and Methods for Automating Validation and Quantification of Interview Question Responses," filed Jan. 29, 2020. This application is related to the following patent applications: U.S. Patent Application Ser. No. 62/967,443, entitled "Systems and Methods for Automatic Candidate Assessments in an Asynchronous Video Setting," filed Jan. 29, 2020 and U.S. patent application Ser. No. 17/160,131, entitled "Systems and Methods for Automatic Candidate Assessments in an Asynchronous Video Setting," filed Jan. 27, 2021. Each of the above identified applications is hereby incorporated by reference in its entirety.

BACKGROUND

Job interviews are one of the oldest and most used employee selection methods Classically, an interview consists of a face to face conversation between the candidate and one or more interviewers. During the conversation, the interviewer tries to obtain genuine information about the candidate's skills and suitability for the job in order to make the right employment decision. The candidate, on the other side, is trying to show they are well suited to fill the vacant position. Due to its conversational and structurally conflictual nature, the job interview has to be described as an interactional event.

Technology deeply impacts the way we interact with others. Throughout history new communication channels have shaped personal interactions and—with the advent of internet and mobile technology—this development has become even faster and more pervasive. Job interviews have not been the exception and have been adapted to new technologies to benefit from reduced costs and increased efficiency. Telephone interviews and video conferences are both well-known examples of the use of technology in job interview settings.

Video interviews can be one-way or two-way interactions. In a one-way video asynchronous video interview (AVI), the applicant does not interact with a live interviewer. Interview questions are presented virtually on a computer, tablet, or smartphone with webcam and audio capabilities. The applicant goes through a series of questions, presented one by one, to which they must immediately respond verbally within a given time limit. However, with all human evaluation mechanisms, it is impossible to remove bias from the reviewers' evaluations of candidates. Further, processing interview video data requires vast amounts of processing resources and/or processing time on a computing level as well as vast amounts of manual human resources, which make automating the process of conducting fully automated video interviews very difficult. The present inventors have identified these difficulties with one-way video interview and assessment systems, and the present disclosure is directed to systems and methods of video assessment that do not suffer from these deficiencies.

SUMMARY OF ILLUSTRATIVE EMBODIMENTS

In some embodiments, systems and methods for automating candidate video assessments include receiving a video submission from a candidate for an available position including one or more baseline response video segments and one or more question response video segments responding to one of a plurality of interview questions. One or more of the interview questions can be close-ended questions. The system can determine, based on one or more nonverbal features detected within the one or more baseline response video segments, a baseline prosody score and a baseline facial expression score for the candidate. For each of the interview questions, the system can detect candidate response attributes from the question response video including a response direction, a response speed, one or more prosodic features, and one or more facial expression features. A prosodic score and a facial expression score can be calculated for each question from the one or more prosodic features and the one or more facial expression features, which can be combined into a nonverbal reaction score. A continuous response score reflecting a strength of the response can be calculated from the response direction and response speed, and a trustworthiness of a candidate response can be determined based on a correspondence between the continuous response score and the nonverbal reaction score. The system can determine, in real-time based on a benchmarked version of the continuous response score, a next interview question for presenting to the candidate at the remote computing device. The system can present, to a second remote computing device of a second party response to receiving a request to view candidate interview results, overall candidate scores reflecting the trustworthiness of the candidate response to each of the plurality of interview questions.

The forgoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1:
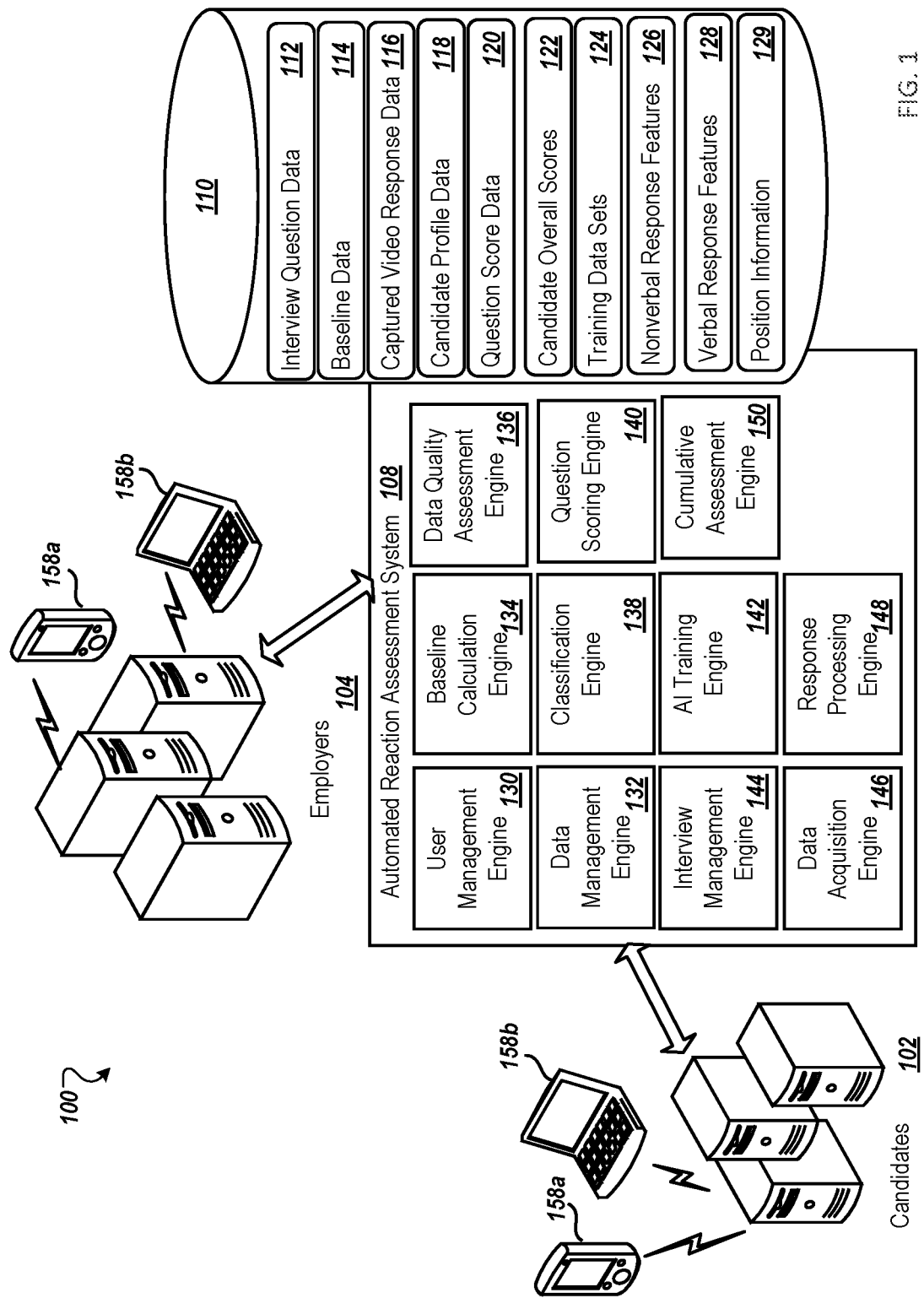
FIG. 1 is a block diagram of an example environment for an automated reaction assessment system.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Aspects of the present disclosure are directed to systems and methods for automating and quantifying interview question responses. In some implementations, employers may interact with a completely automated, computer-implemented candidate interviewing system that is configured to detect candidate responses by analysis of features extracted from video data. In addition to detecting the response to the interview question, the system can also determine relative attributes of the response, which can be used to determine subsequent interview questions in real-time and on-the-fly. In some embodiments, in addition to the actual response (e.g., yes/no, agree/disagree, enjoy/dislike, etc.), the relative attributes can include response speed and response strength as compared to baseline attributes for the candidate. In some implementations, the questions that the candidate answers are close-ended (e.g., positive-negative (binary) or positive-negative-neutral (ternary)) questions where the system determines the candidate's response based on head movement, facial expression, and/or prosody using audio, video, and/or image processing techniques. In some aspects, close-ended questions can also include other types of questions that have a finite set of possible single-phrase answers (e.g., answers to the question, "Which color do you like better: red or blue?"). In some examples, the system can apply a specially trained machine learning classifier that can detect one or more response attributes from the captured video data. In some examples, upon receipt of a candidate response to an interview question, the system may determine a next close-ended (e.g., yes/no, agree/disagree/neutral, etc.) question based on the previous question response. Being able to select interview questions on-the-fly based on verbal and nonverbal attributes of candidate responses reduces the overall number of questions that have to be asked since the system can determine which questions are most applicable to the candidate and the available position the candidate is interviewing for based on the candidate responses. Further, being able to use auxiliary data available in detected nonverbal attributes allows the system to more efficiently detect how trustworthy a given candidate's response is without a human having to manually review the video data of the interview.

In some implementations, the automated system for detecting and quantifying candidate interview responses can also process open-ended interview questions that can have more than two or three possible responses. In some examples, the system may generate a series of close-ended questions for the candidate to respond to. Once the system has received responses from the interviewee for all applicable questions in a set of one or more close-ended interview questions, the system can generate an open-ended question for the interviewee to respond to. Upon receiving the video data of the candidate response to the open-ended video question, the system can analyze the content of the open-ended question response. In some examples, the system can apply a trained speech-to-text algorithm and natural language classifier to determine how well the candidate fits one or more ideal personality characteristics for the available position. In one example, the system can apply the open-ended question processing, scoring, and data quality assessment techniques to identify personality aspects as described in U.S. Provisional Application Ser. No. 62/967,443, entitled "Systems and Methods for Automatic Candidate Assessments in an Asynchronous Video Setting" and filed on Jan. 29, 2020, the contents of which are fully incorporated herein by reference.

In some embodiments, generating a series of close-ended questions on-the-fly, based on attributes of candidate responses, enables the system to determine a best fit open-ended question to ask the candidate. In some implementations, processing and analysis of open-ended question response data for multiple questions is computationally intensive and can either take a long amount of time to process or use a vast amount of processing resources in order to deliver real-time results. By implementing the methods described further herein, the automated system can save vast amounts of processing time and processing resources, thus making the systems and methods described herein a technical solution to a technical problem. For example, by generating a series of customized close-ended questions on-the-fly, the system is also able to determine an open-ended question for asking the candidate that is customized based on the candidate's previous answers to the close-ended questions. The system can use the close-ended questions that are less computationally expensive to process to identify a best-fit open-ended question that allows the system to get the most valuable information from the candidate. Additionally, the system does not have to waste computational resources processing open-ended question responses that may not provide detectable personality aspect features that can be used to assess whether the candidate is well-suited to the position. Therefore, by generating a series of customized close-ended questions in real-time and on-the fly and processing the responses in real-time, the system is able to provide the benefit of having to generate fewer computationally intensive open-ended interview questions. Additionally, by strategically generating interview questions on-the-fly based on previous responses from the candidate, the system can gather more information in a shorter period of time than other conventional systems. In one example, an interview process managed by the system as described herein takes a candidate approximately ten minutes to complete.

FIG. 1 is a diagram of an example environment 100 for an automated reaction assessment system 108. The diagram illustrates relationships, interactions, computing devices, processing modules, and storage entities used to gather, generate, organize, store, and distribute the information necessary to automatically, accurately, and efficiently process interview question responses received from candidates for one or more available jobs without any bias that comes from human input. In some implementations, the automated reaction assessment system 108 can provide employers 104 with the ability to define customized competency descriptions for one or more available jobs and identify interview questions associated with the defined job competencies. The system 108, in some embodiments, automatically converts the identified job competencies and interview questions into customized interview mappings that map the questions and competencies onto a set of personality aspects associated with a personality model.

When a candidate 102 submits video responses to the identified interview questions, the automated reaction assessment system 108, in some implementations, generates question response transcripts by performing speech-to-text conversion on an audio portion of each of the video files to create interview question transcripts. In some examples, a natural language classifier can be specifically trained to detect positive and negative polarizations of the personality aspects from the personality model within an interview question transcript. In some embodiments, the automated reaction assessment system 108 uses detected occurrences of each of the personality aspects in each of the interview question transcripts to compute scores for each of the personality aspects. Based on the computed scores, in some examples, the system 108 can determine how well suited a candidate is, or how much aptitude the candidate has, for a particular job.

In certain embodiments, candidates 102 may connect to the automated reaction assessment system 108 via a number of computing devices distributed across a large network that may be national or international in scope. The network of candidates 102 can be separate and independent from networks associated with other entities in the video assessment environment 100, such as the providers 104. In addition, the data handled and stored by the candidates 102 may be in a different format than the data handled and stored by the other entities of the video assessment environment 100. The candidates 102 may include, in some examples, prospective and actual job applicants for any available jobs created in the system 108 by employers 104.

Employers 104, in some implementations, include a number of computing devices distributed across a large network that may be national or international in scope. The network of employers 104 can be separate and independent from networks associated with other entities in the video assessment environment 100, such as the candidates 102. In addition, the data handled and stored by the employers 104 may be in a different format than the data handled and stored by the other participants of the video assessment environment 100. In some implementations, the employers 104 can include large-scale or small-scale companies who wish to use the automated reaction assessment system 108 to automatically screen and score candidate video interview submissions. In some examples, the employers 104 interact with one or more system-generated user interface screens to identify interview questions and define ideal competencies, attributes, and personality traits of an ideal employee that can be used by the system to automatically assess how well suited a particular candidate is for a job.

In some embodiments, the automated reaction assessment system 108 may include one or more engines or processing modules 130, 132, 134, 136, 138, 140, 142, 146 that perform processes associated with generating personality aspect mappings to questions for available positions and performing video assessments of submitted candidate interview videos based on the generated personality aspect mappings. In some examples, the processes performed by the engines of the automated reaction assessment system 108 can be executed in real-time to provide an immediate response to a system input such as a request by an employer 104 and/or candidate 102 to obtain processed information from the system 108. For example, the system 108 can convert video submissions to text transcripts, detect personality aspects from a personality model using a trained natural language classifier, and score candidate interview responses in real-time in response to receiving a candidate video interview submission.

In some implementations, the automated reaction assessment system 108 may include a user management engine 130 that may include one or more processes associated with providing an interface to interact with one or more users (e.g., individuals employed by or otherwise associated with employers 104 as well as candidates 102) within the video assessment environment 100. For example, the user management engine 130 can control connection and access to the automated reaction assessment system 108 by the candidates 102 and employers 104 via authentication interfaces at one or more external devices 158. In some examples, the external devices 158 may include, but are not limited to, personal computers, laptop/notebook computers, tablet computers, and smartphones. In some implementations, the user management engine 130 controls which system data is displayed to which system user. For example, the user management engine 130 may associate candidate interview responses with an available position for a particular employer 104 such that only information associated with jobs submitted by the respective employer 104 are displayed for viewing and feedback by a particular employer 104 based on received authentication credentials. Additionally, the user management engine 130 can be configured to authenticate candidates 102 accessing the system 108 to apply for one or more available positions. For example, when a candidate accesses an interview question interaction user interface (UI) screen 400 (see FIG. 4), the user management engine 130 can authenticate the candidate 102 using login credentials (e.g., username and password) and/or captured biometric information (e.g., facial features, iris pattern, voice characteristics) to validate and/or confirm the identity of the candidate 102.

The automated reaction assessment system 108, in some examples, may also include a data management engine 132 that organizes, stores, and controls access to data in data repository 110. For example, in response to receiving position information data inputs from an employer 104, the data management engine 132 can store the data inputs as a portion of the position information 129 for the respective position. In some implementations, the data management engine 132 can also link all information related to an interview for a particular candidate interview within data repository 110. For example, the data management engine 132 can link the questions from the interview question data 112 that were asked of the candidate 102 to the position information 129 along with question scores 120, candidate overall scores 122, and baseline data 114 to candidate profile data 118 that provides biographical and experiential information about the candidate (e.g., demographic information, contact information, education experience, work experience and locations) as well as benchmarked trustworthiness and continuous response scores for the candidate 102 and other groups of candidates sharing similar attributes (e.g., language and cultural similarities). Additionally, the data management engine 132 can also be configured to compile updated training data (for example, from newly calculated question scores and submitted feedback from employers) into the training data sets 124. In some implementations, the data management engine 132 can also link captured nonverbal response features 126 (e.g., facial expression and prosodic features) and verbal response features 128 (e.g., speed/latency of the response along with the response) to the respective interview question data 112, question scores 120 and candidate profile data 118.

The system 108, in some implementations, can also include an interview management engine 144 that controls front-end processing of a candidate interview process. For example, the interview management engine 144 can interface with data acquisition engine 146, response processing engine 148, and/or baseline calculation engine 134 to cause presentation of information at one or more UI screens provided to candidates 102 and/or employers 104 as well as collection of information provided by the candidates 102 and/or employers 104. In some embodiments, the interview management engine 144, in some examples in conjunction with data acquisition engine 146, can capture video data during a calibration portion of a candidate interview, which can be stored in data repository 110 as captured video response data 116. In one example, the interview management engine 144 can generate a series of directions or questions to the candidate 102 to prompt them to provide one or more baseline close-ended (yes/no) question responses. For example, the interview management engine 144 can generate prompts for the candidate 102 to provide a "yes" or "no" answer at different speeds (quickly, slowly, normal speed) or to just provide a nonverbal response.

In some examples, the interview management engine 144, together with data acquisition engine 146, can also present interview questions and capture candidate video responses to one or more interview questions, which are determined in real time by response processing engine 148. In some implementations, the interview management engine 144 controls the presentation of interview questions at a UI screen and monitors whether the candidate 102 responds to the questions within predetermined limits. In some implementations, the interview questions can include close-ended questions or a combination of close-ended and open-ended questions. As discussed further herein, in some examples, the interview management engine 144 can present a set of one or more close-ended questions followed by an open-ended question identified by response processing engine 148 based on attributes (verbal and/or nonverbal attributes) of the candidate's responses to the presented interview questions.

Figure 4:
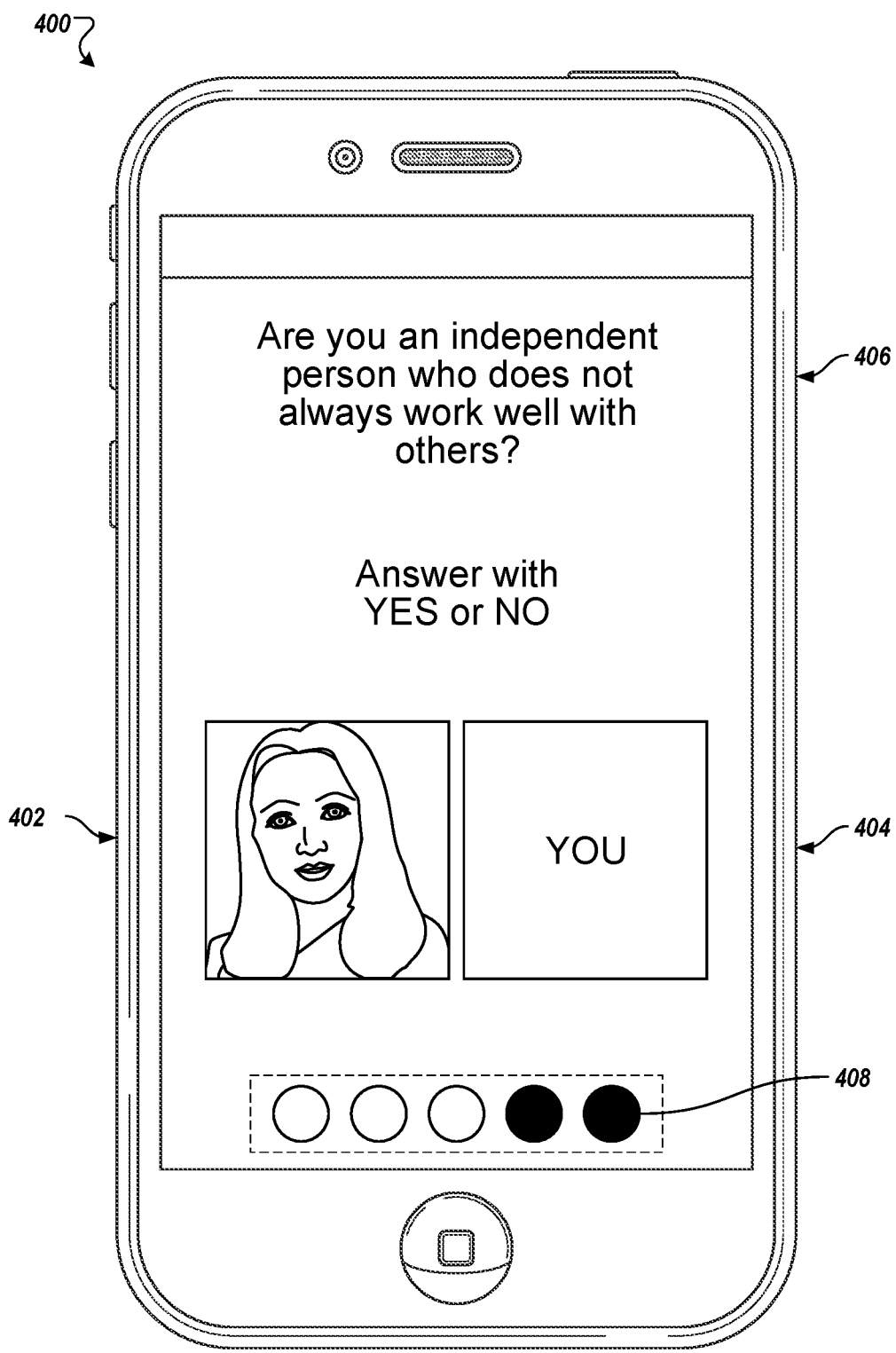
FIG. 4 illustrates an interview question interaction user interface screen.

For example, FIG. 4 illustrates an example of an interview question interaction user interface (UI) screen 400 that allows the candidate 102 to interact with the automated reaction assessment system 108 to provide responses to one or more close-ended interview questions presented at the UI screen 400. In other examples, the interview question interaction UI screen 400 can also provide open-ended questions for the candidate 102 to respond to. In some embodiments, an interview management engine (e.g., interview management engine 144 in FIG. 1) can generate a customized video avatar 402 presented within the UI screen 400 that functions as the "interviewer" of the candidate 102 by speaking the questions to the candidate 102. In some examples, the employer 104 and/or candidate 102 can design the features of the avatar (gender, facial features, voice). In some examples, a video capture window 404 can be presented in the same UI screen 400, which displays the video data being captured by the system 108 as the candidate 102 responds to the interview questions.

In some implementations, the interview management engine 144 can obtain baseline verbal (e.g., speed and latency of response) and nonverbal (e.g., facial expression and prosody) data from the candidate 102 via the UI screen 400. In one example, the avatar 402 begins the interview process by explaining the purpose and execution of the interview process the candidate is going through and guides the candidate through providing a variety of types of close-ended responses. For example, the avatar 402 can instruct the candidate 102 to provide "yes" or "no" responses slowly, quickly, or at a normal speed. In other examples, the avatar 402 may instruct the candidate 102 to provide just a verbal response and/or to also provide nonverbal indications of the response (e.g., nodding or shaking the head).

In addition to the question being spoken to the candidate 102 via the avatar 402, the question 406 can also be presented visually to the candidate 102 at the UI screen 400. Additionally, the UI screen 400 can also include a visual timer 408 that provides a visual indicator to the candidate 102 of how much time remains for the candidate 102 to provide a response to the question. In one example, the visual timer 408 includes a visual countdown with dots that change color as time elapses. The amount of time can be set to a predetermined maximum allowable time for the candidate 102 to answer each of the questions. If the time allotted at the visual timer 408 lapses, then the UI screen 400 may present an alert to the candidate 102 that he failed to provide a response to the question in the predetermined period of time. In one example, the predetermined period of time is 5 seconds. If an overall interview time is 10 minutes, the interview management engine can present up to 120 items (calibration questions and interview questions) to the candidate 102. If the candidate 102 fails to respond to more than a predetermined number of questions within the time period, the system 108 may abort the interview. Once the candidate 102 provides a response to the question, the interview management engine 144 detects the response and automatically presents the next question. Further, once an interview question response is detected, the data acquisition engine 146 captures the video data associated with the response, processes the data, which can include separating an audio portion from a video portion of the data file, and saving the processed video data in the data repository 110 as captured video response data 116.

Returning to FIG. 1, the automated reaction assessment system 108 can also include a data acquisition engine 146 that controls, processes, and manages the interview submissions received from candidates 102 applying for available positions of one or more employers 104. In the calibration portion of the interview, in some embodiments, the data acquisition engine 146 can capture and extract one or more baseline candidate attributes (e.g., facial expression and/or prosodic features) that can be used to automatically assess whether the candidate's responses during the interview are trustworthy and/or consistent with the typical responses of the candidate 102. In some examples, the captured prosodic features can include voice inflection, tone, intonation, stress, rhythm, and pronunciation of the response. The captured facial expression features can include visual indications of moods and/or behaviors such as happiness, sadness, surprise, neutral, anger, contempt, and disgust. The data acquisition engine 146 can also extract response features from the candidate responses to the baseline prompts that can factor into a benchmarked latency for the candidate 102 and/or other candidates with similar language and/or cultural attributes. In some implementations, the data acquisition engine 146 can extract the one or more baseline candidate attributes from a subset of captured frames. In some examples, the data acquisition engine 146 can transmit the captured baseline candidate attributes to baseline calculation engine 134 for processing.

In addition, the data acquisition engine 146 can also capture verbal and nonverbal features of candidate responses to interview questions. In some implementations, when a candidate responds to an interview question presented by the interview management engine 144, the data acquisition engine 146 can extract verbal response features 128 and nonverbal response features 126 from the captured video data, which can be stored in the data repository 110. The verbal response features 128, in some implementations, can include one or more video frames indicating a speed and direction of the response (e.g., yes/no/neutral). The nonverbal response features 126, in some examples, the nonverbal response features 126 can include one or more video frames indicating facial expressions and/or prosodic features of the response. The captured facial expression features can include visual indications of moods and/or behaviors such as happiness, sadness, surprise, neutral, anger, contempt, and disgust. The captured prosodic features can include voice inflection, tone, intonation, stress, rhythm, and pronunciation of the response. In some embodiments, the data acquisition engine 146 can transmit the captured response attributes to question scoring engine 140 for processing.

In some embodiments, the automated reaction assessment system 108 includes a baseline calculation engine 134 that calculates baseline reaction scores for the candidate 102 from baseline features captured by data acquisition engine 146 during the calibration process. In some examples, the baseline calculation engine 134 discards outlier video frames and calculates a baseline facial expression score and a baseline prosody score for the candidate from averages of the retained frames. In one example, the baseline scores fall in a range from −1 to 1, where −1 represents a negative response, 0 represents a neutral response, and 1 represents a positive response. The baseline calculation engine 134 can store the baseline scores in the data repository as baseline data 114.

The automated reaction assessment system, in some implementations, can also include a question scoring engine 140 that computes scores for each of the interview question responses provided by the candidate 102, which can be stored in data repository 110 as question score data 120. In some examples, the question scoring engine 140 can compute a continuous response score that reflects the direction (yes/no/neutral) and speed (e.g., latency) of the candidate response for the respective question. In one example, the continuous response score is the product of the direction (−1 if the response is no, and 1 for all other responses) multiplied by a speed of the response, which can be normalized to a scale between 0 and 1. In some embodiments, the question scoring engine 140 can also compute nonverbal scores for each question response, which can include a facial expression score and a prosody score. In some examples, the question scoring engine 140 discards outlier video frames and calculates a facial expression score and a prosody score for the candidate from averages of the retained frames. In one example, the scores can fall in a range from −1 to 1, where −1 represents a negative response, 0 represents a neutral response, and 1 represents a positive response. Additionally, the facial expression score and prosody score can be further adjusted by subtracting values for the respective baseline facial expression score or baseline prosody score.

In some examples, the question scoring engine 140 can calculate a nonverbal reaction score for each question using the prosody score and/or the facial expression score. In some examples, a raw nonverbal score reflecting both the facial expression score and the prosody score can be benchmarked against language and culture-dependent norms for the candidate 102, which can be determined from the candidate profile data 118. Additionally, the raw nonverbal score can be normalized to a value between −1 and 1. Using the nonverbal reaction score and the continuous response score, in some embodiments, the question scoring engine 140 can calculate a raw trustworthiness score for the question, which can indicate how well the candidate's nonverbal reaction agrees with the verbal response. The question scoring engine 140 can also normalize the trustworthiness score to a stanine score between 1 and 9 where 1 indicates a lowest amount of trustworthiness and a 9 reflects a highest amount of trustworthiness. For example, if a candidate 102 provides "yes" to a question asking whether the candidate works well with others, but the candidate's detected facial expression is "angry" and the prosodic features also indicate anger and/or uncertainty (sharp, loud tone), then the calculated trustworthiness score may be low, indicating that the candidate's response is not trustworthy. However, if the candidate responds "yes" to a question asking whether the candidate 102 meets minimum education requirements, the facial expression features indicate happiness, and the prosodic features indicate confidence (steady tone, steady inflection in voice), then the trustworthiness score can be toward a higher end of the stanine scale. For any open-ended questions presented to the candidate 102, the question scoring engine 140 can apply the question scoring techniques described in U.S. Provisional Application Ser. No. 62/967,443, entitled "Systems and Methods for Automatic Candidate Assessments in an Asynchronous Video Setting" and filed on Jan. 29, 2020, the contents of which are fully incorporated herein by reference.

In some implementations, the automated reaction assessment system 108 can also include a response processing engine 148 that processes a candidate's response to an interview question in real-time and determines a next question to present to the candidate 102 on-the-fly based on the candidate's previous response. In some examples, the speed of the candidate's response can be benchmarked against language-dependent norms indicated in the candidate profile data 118 associated with the respective candidate 102 who is interviewing for the position so that candidates of a type of cultural/language background are not favored more than other cultures that may not have speech patterns that are as fast. Additionally, the response processing engine 148 can also perform intra-individual norming of response speeds to not advantage or disadvantage those who are overall faster or slower at responding. Based on the benchmarked speed of response and the direction of the response (yes/no/neutral), the response processing engine 148 can determine a next question for the interview management engine 144 to present to the candidate 102.

As discussed further below, the response processing engine 148 can identify the next question from the stored interview question data 112. For example, if a candidate 102 responds quickly with a "yes" to a question asking whether the candidate meets minimum educational requirements for the position, then the response processing engine 148 may identify the next question to be a question directed toward work experience and/or interpersonal communication skills. In some implementations, after selecting a series of close-ended questions, the response processing engine 148 may select an open-ended question to present to the candidate 102. By using the candidate's previous response attributes (both verbal and nonverbal) to multiple questions to select a targeted open-ended question that is customized to the candidate 102, the system 108 can gather as much or more information from fewer open-ended questions. Processing open-ended questions (e.g., converting speech to text, applying a natural language classifier to detect key features, scoring the question responses) can consume more processing resources than processing open-ended questions. Therefore, being able to characterize electronically detectable, nonverbal attributes of close-ended question responses as described herein to strategically select both close-ended and open-ended questions for a candidate 102 to respond to provides a technical solution to the technical problem of providing a fully automated system for conducting candidate interviews in a processing efficient manner that requires no human interaction.

In some implementations, the automated reaction assessment system 108 can also include a cumulative assessment engine 150 that calculates overall response and trustworthiness scores for a candidate interview and generates reports for presentation to employers 104. In some examples, the overall trustworthiness and response scores can provide single score indicators of how well suited a candidate is for a particular job and/or how trustworthy the candidate's responses are. In one example, the overall trustworthiness score can be an average of the trustworthiness scores for all the close-ended question responses provided by the candidate 102. In some embodiments, the overall response score for the candidate 102 can be an average of the continuous response scores for the close-ended question responses provided by the candidate 102. The overall trustworthiness and response scores can be provided to employers 104 via one or more reports generated by the cumulative assessment engine 150. In some examples, the reports can rank a respective candidate 102 against other candidates 102 applying for the same position with respect to trustworthiness scores and/or continuous response scores.

In some implementations, the automated reaction assessment system 108 can include a data quality assessment engine 136 that determines whether the candidate responses meet predetermined quality standards that can be depended on by employers 104 for making hiring decisions. In some examples, if the overall trustworthiness score and/or one or more trustworthiness scores for individual questions fall below a predetermined threshold, the data quality assessment engine 136 may reject the interview submission and/or prompt the candidate 102 to provide a new set of interview question responses. In some examples, for any open-ended questions presented to the candidate 102, the data quality assessment engine 136 can apply the data quality assessment techniques described in U.S. Provisional Application Ser. No. 62/967,443, entitled "Systems and Methods for Automatic Candidate Assessments in an Asynchronous Video Setting" and filed on Jan. 29, 2020, the contents of which are fully incorporated herein by reference.

The automated reaction assessment system 108, in some implementations, can also include a classification engine 138 that is configured to apply one or more trained machine learning algorithms to classify one or more detected facial expression features and/or prosodic features as being associated with a positive (yes), neutral, or negative (no) response to a close-ended question. In some examples, the classification engine 138 can be trained to detect facial features associated with one or more emotional expressions such as happiness, sadness, surprise, neutral, anger, contempt, and disgust. The features associated with each of the detectable expressions can include shape and movement of eyes, pupil size, facial wrinkles (e.g., around eyes and mouth), lips/mouth, and/or cheeks. The classification engine 138, in some examples, can be trained by artificial intelligence (AI) training engine 142 with training data sets 124 of facial features that can be updated over time as the system 108 processes interview responses for candidates 102. In some examples, the classification engine 138 can also be trained to associate detected facial expression features associated with a response value in a predetermined range (e.g., $-1$ to 1) such that detections of the same facial expression may be assigned different scores based on the shape, size, and/or magnitude of movement of detected facial features associated with a respective expression. For example, detected features associated with a large smile may be assigned a higher positive score (e.g., closer to 1) than a smaller or more neutral smile (e.g., closer to 0). In some examples, the question scoring engine 140 and/or baseline calculation engine 134 can determine the respective facial expression scores for a candidate based on the facial detection features identified by the classification engine 138.

Additionally, in some implementations, the classification engine 138 can also be trained by the AI training engine 142 to detect prosodic features associated with variations of positive (yes), neutral, and negative (no) responses in captured video frames. The detectable prosodic features, in some implementations, can include intonation, stress, and rhythm of speech of a respective candidate response. The classification engine 138, in some examples, can be trained by artificial intelligence (AI) training engine 142 with training data sets 124 of prosodic features that can be updated over time as the system 108 processes interview responses for candidates 102. In some examples, the classification engine 138 can also be trained to associate detected prosodic features associated with a response value in a predetermined range (e.g., $-1$ to 1) such that it can detect an amount of variation in prosodic features associated with variable magnitudes of response. For example, detected prosodic features associated with a large amount of uncertainty (e.g., upward inflection of the voice at the end of a response) can be associated with a more negative score (e.g., closer to −1) than a smaller amount of uncertainty (e.g., closer to 0) associated with a smaller magnitude of upward inflection of the voice at the end of the response. In some examples, the question scoring engine 140 and/or baseline calculation engine 134 can determine the respective prosodic scores for a candidate based on the prosodic features identified by the classification engine 138.

In some examples, the classification engine 138 can also include a natural language classifier configured to detect one or more personality traits of a candidate 102 in transcripts of responses to open-ended questions as described in U.S. Provisional Application Ser. No. 62/967,443, entitled "Systems and Methods for Automatic Candidate Assessments in an Asynchronous Video Setting" and filed on Jan. 29, 2020, the contents of which are fully incorporated herein by reference.

In some implementations, the automated reaction assessment system 108 can also include an AI training engine 142 that trains the machine learning classifiers (facial expression, prosody, natural language) of the classification engine 138. In some examples, the AI training engine 142 uses customized training data sets 124 to train each of the machine learning classifiers to detect nonverbal features (e.g., facial expression features and prosodic features) within video data capturing candidate responses to close-ended questions. The AI training engine 142 can also compile customized training data sets 124 for training a natural language classifier to detect personality traits of the candidate 102 within transcripts of open-ended questions as described in U.S. Provisional Application Ser. No. 62/967,443, entitled "Systems and Methods for Automatic Candidate Assessments in an Asynchronous Video Setting" and filed on Jan. 29, 2020, the contents of which are fully incorporated herein by reference.

In some examples, the AI training engine 142 can augment with training data sets 124 with new data for training the nonverbal feature detection classifiers after receiving and processing each set of candidate video responses to a close-ended question set. Additionally, the training data sets 124 can also include amplifying feedback provided by employers 104 regarding the accuracy of the scores determined from the detected nonverbal features.

Figure 2:
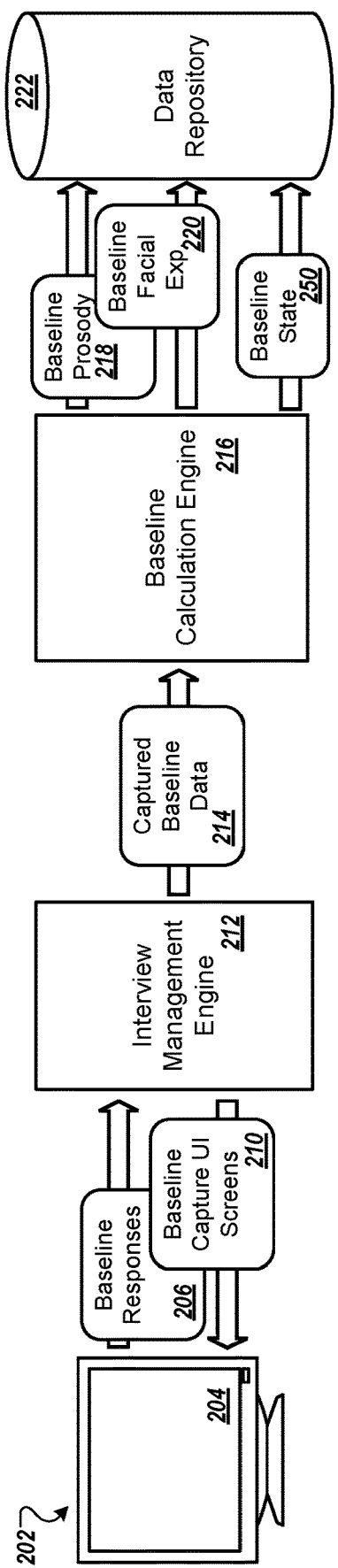
FIGS. 2-3 illustrate data work flows for an automated reaction assessment system.

Turning to FIG. 2, a workflow diagram of a candidate baseline determination process 202 is illustrated. In some implementations, an interview management engine 212 provides a series of baseline capture UI screens 210 to an external device 204 of a candidate applying for one or more positions managed by an automated reaction assessment system (e.g., automated reaction assessment system 108 in FIG. 1). The baseline capture UI screens 210, in some examples, include a video capture interface that allows the interview management engine 212 to capture baseline features (e.g., mood, facial expressions, baseline responses to close-ended questions) of the candidate responses 206 as the candidate responds to question prompts. For example, the baseline capture UI screens 210 can include multiple variations of yes/no baseline capture prompts, which may instruct the candidate to speak the word "yes" or "no," indicate a "yes" or "no" responses by moving the head (e.g., nodding or shaking head), or both speaking and moving the head simultaneously. In some examples, the interview management engine 212 can prompt the candidate to respond to the prompts quickly, slowly, or at an average speed. In one example, the interview management engine 212 can generate six or more variations of yes/no baseline capture prompts for presentation to the candidate 102 via the user interface screen.

In some examples, the interview management engine 212 can extract verbal and nonverbal features from the captured baseline responses 206, which can be passed to baseline calculation engine 216 as captured baseline data 214. For example, the captured baseline data can include detected facial expression and prosodic features in one or more frames of the baseline responses 206. In some examples, the baseline calculation engine 216 computes a baseline prosody score 218 and a baseline facial expression score 220, which can be stored in data repository 222 for use in calculating trustworthiness scores for each of the close-ended question responses. In some examples, the baseline calculation engine 216 computes a baseline state score 250 based on the mood survey data 508 which can be stored in data repository 222 for potential use in calculating but not exclusively baseline scores, continuous response scores, and overall trustworthiness and response scores (see FIGS. 3 and 5). In some examples, the baseline state score captures an overall mood or emotional state of the candidate during the interview and can be based on detected facial expression and other mood-based features. In some embodiments, the mood-based features can include detected facial expression features and other physiological features that can indicate a level of calm/peacefulness or agitation/nervousness/anger of the candidate (e.g., respiratory rate can indicate a level of agitation or nervousness). The baseline state score can be used to normalize the other scores calculated by the system 108 based on mood indicators that are customized to both the individual and the particular interview. For example, a given candidate can have different baseline state scores in different interviews based on changes in mood of the candidate. In some examples, the baseline calculation engine 216 discards outlier video frames and calculates a baseline facial expression score and a baseline prosody score for the candidate from averages of the retained frames. In one example, the baseline scores 218, 220 fall in a range from −1 to 1, where −1 represents a negative response, 0 represents a neutral response, and 1 represents a positive response.

Figure 3:
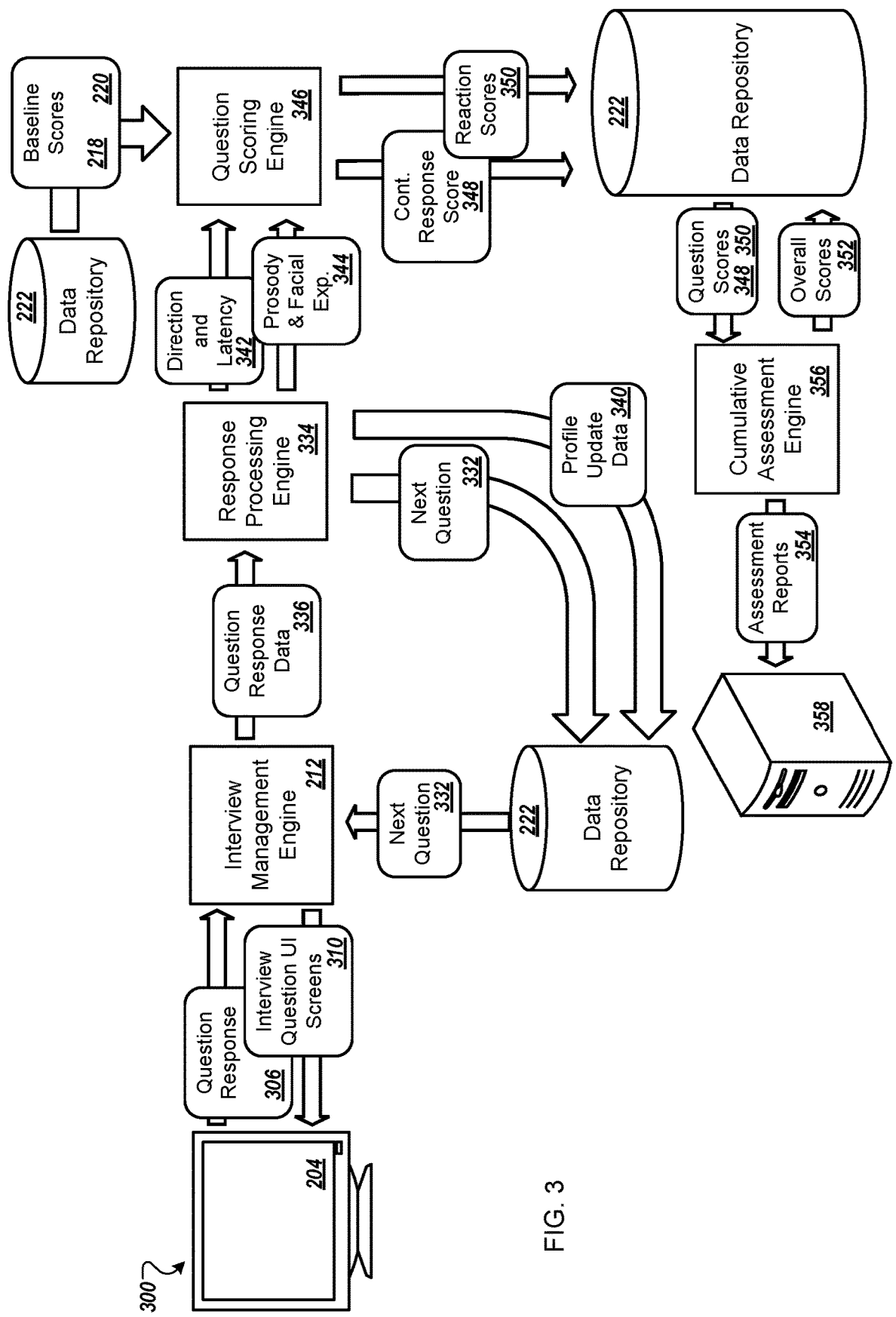

Turning to FIG. 3, a workflow diagram of an automated reaction assessment process 300 is illustrated. In some implementations, the interview management engine 212 provides a series of interview question capture UI screens 310 to the external device 204 of the candidate applying for one or more positions managed by an automated reaction assessment system (e.g., automated reaction assessment system 108 in FIG. 1). The interview question capture UI screens 310, in some examples, include a video capture interface that allows the interview management engine 212 to capture nonverbal and verbal features of candidate responses to interview questions 306. One example of an interview question capture UI screen 310 is the interview question interaction UI screen 400 shown in FIG. 4. The interview question responses 306 can include both close-ended question responses and open-ended question responses. The interview management engine 212, in some embodiments, can access next question data 332 for presenting in the interview question UI screens from data repository 222. The next question data 332 can be determined on-the-fly and in real-time by the response processing engine 334 based on previous question responses provided by the candidate. In some examples, the interview management engine 212 can extract detectable features from the video and/or audio data of the interview question responses, which can include prosodic features and facial expression features from one or more frames of the response. Additionally, the detectable features can include one or more video frames that indicate the candidate's speed and direction of response. The interview management engine 212, can transmit the detected features as question response data 336 to response processing engine 334.

In some embodiments, the response processing engine 334 can determine response-based features (direction and latency of the response 342) and nonverbal reaction-based features (prosody and facial expression 344) from the question response data 336. Additionally, the response processing engine 334 can process a candidate's response to an interview question in real-time and can determine a next question 332 on-the-fly based on the candidate's previous response. In some implementations, the response processing engine 334 (e.g., such as the response processing engine 148 of FIG. 1), after selecting a series of close-ended questions, may select an open-ended question to present to the candidate 102. For example, the speed of the candidate's response can be benchmarked against language-dependent norms indicated by demographic information regarding the respective candidate 102 (e.g., retained in the candidate profile data). In this manner, for example, one candidate's cultural and/or language background will not be favored over other cultures/languages with differently paced speech patterns. Additionally, the response processing engine 334 can also perform intra-individual norming of response speeds to not advantage or disadvantage those who are overall faster or slower at responding, which can also be used in determining the next question 332. Further, the response processing engine 334 can generate profile update data 340 from the intra-individual norming data and benchmarking data that can be stored in data repository 222 and used in processing future responses.

In some examples, question scoring engine 346 can use the direction and latency of the response 342, extracted prosody and facial expression features 344, and baseline facial expression and prosody scores 218, 220 to determine a continuous response score 348 and nonverbal reaction score 350 for each question. In some examples, the question scoring engine 346 can compute a continuous response score 348 that reflects the direction (yes/no/neutral) and speed (e.g., latency) of the candidate response for the respective question. In one example, the continuous response score is the product of the direction (−1 if the response is no, and 1 for all other responses) multiplied by a speed of the response, which can be normalized to a scale between 0 and 1. In some embodiments, the question scoring engine 346 can also compute nonverbal reaction scores 350 for each question response, which can include a facial expression, a prosody score, a nonverbal reaction score, and a question trustworthiness score. In some examples, the question scoring engine 346 discards outlier video frames and calculates a facial expression score and a prosody score for the candidate from averages of the retained frames. In one example, the scores fall in a range from −1 to 1, where −1 represents a negative response, 0 represents a neutral response, and 1 represents a positive response. Additionally, the facial expression score and prosody score can be further adjusted by subtracting values for the respective baseline facial expression score 220 or baseline prosody score 218.

In some examples, the question scoring engine 346 can also calculate a nonverbal reaction score for each question using the prosody score and/or the facial expression score. In some examples, a raw nonverbal score reflecting both the facial expression score and the prosody score can be benchmarked against language and culture-dependent norms for the candidate, which can be determined from the candidate profile data. Additionally, the raw nonverbal score can be normalized to a value between −1 and 1. Using the nonverbal reaction score and the continuous response score, in some embodiments, the question scoring engine 346 can calculate a raw trustworthiness score for the question, which can indicate how well the candidate's nonverbal reaction agrees with the verbal response. The question scoring engine 346 can also normalize the trustworthiness score to a stanine score between 1 and 9 where 1 indicates a lowest amount of trustworthiness and a 9 reflects a highest amount of trustworthiness.

In some implementations, a cumulative assessment engine 356 can calculate overall response and trustworthiness scores 352 from the individual question scores 348, 350 for a candidate interview and generates assessment reports 354 for presentation to employers 358. In some examples, the overall trustworthiness and response scores 352 can provide single score indicators of how well suited a candidate is for a particular job and/or how trustworthy the candidate's responses are. In one example, the overall trustworthiness score can be an average of the trustworthiness scores for all the close-ended question responses provided by the candidate. In some embodiments, the overall scores 352 for the candidate can be an average of the continuous response scores and trustworthiness scores for the close-ended question responses provided by the candidate. In some examples, the assessment reports 354 can rank a respective candidate against other candidates applying for the same position with respect to trustworthiness scores and/or continuous response scores.

Figure 5:
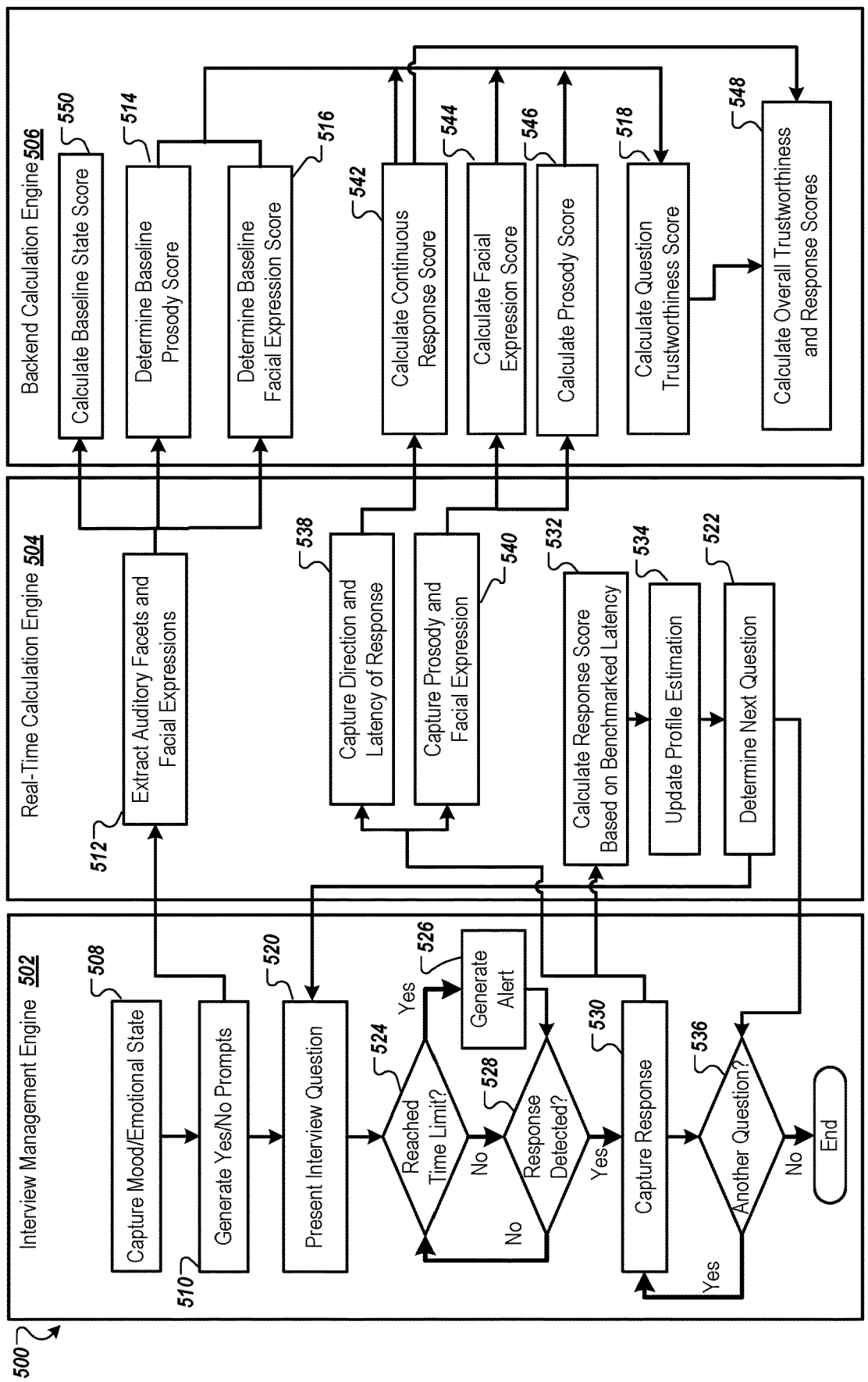
FIG. 5 illustrates a flow chart of an example method for automating a video interview process.

FIG. 5 illustrates a flow diagram of an example method 500 of performing an automated interview of a candidate for an available position. In some examples, different portions of the method 500 can be performed by different sets of processing resources, or engines, of an automated reaction assessment system (e.g., system 108 in FIG. 1). In one example, the engines can include an interview management engine 502, a real-time calculation engine 504, and a back-end calculation engine 506. In some implementations, the engines 502, 504, 506 exchange information with each other when performing the automated interview process 500.

In some implementations, the method 500 begins with the interview management engine 502 capturing a mood and emotional state of a candidate 102 (508). For example, the interview management engine 502 can present a user interface screen through a web and/or application portal to an external device 158 of the candidate 102. Through the user interface screen, in some examples, the interview management engine 502 can capture a mood and/or emotional state of the candidate 102 via a video feed capture interface. In some embodiments, the interview management engine 502 stores the video data capturing the mood and/or emotional state of the candidate 102 in data repository 110 as part of baseline data 114 for the candidate 102. This captured mood/emotional state video data can be used by the system 108 to determine a baseline facial expression for the candidate 102, which can be used to determine relative response attributes for each question response provided by the candidate 102. In some examples, the user interface screen presented by the interview management engine 502 may prompt the candidate 102 to look at the camera and remain in a neutral state. In other examples, the user interface screen may not provide any direction to the candidate 102 regarding how to act when the mood/emotional state video data is captured.

In some implementations, the interview management engine 502 can also generate a series of yes/no prompts for the candidate to respond to that the system uses to determine baseline response attributes of the candidate 102 (510). For example, the interview management engine 502 may cause an avatar, presented in the user interface screen, to prompt the candidate 102 to say "yes" or "no" whenever the candidate 102 sees the respective word presented on the screen. The interview management engine 502 can generate multiple variations of yes/no baseline capture prompts, which may instruct the candidate 102 to speak the word "yes" or "no," indicate a "yes" or "no" responses by moving the head (e.g., nodding or shaking head), or both speaking and moving the head simultaneously. In some examples, the interview management engine 502 can prompt the candidate 102 to respond to the prompts quickly, slowly, or at an average speed. In one example, the interview management engine 502 can generate six or more variations of yes/no baseline capture prompts for presentation to the candidate 102 via the user interface screen. Upon receiving the captured video data of the responses to the yes/no baseline prompts, the interview management engine 502 can store the captured data as part of the baseline data 114 in data repository 110.

In some implementations, using the video data captured by the interview management engine 502 for the captured mood/emotional state (508) as well as the responses to the baseline yes/no prompts (510), the real-time calculation engine 504 extracts auditory facets and facial expressions of the candidate 102 (512). In some implementations, the extracted auditory facets can include voice inflection and tone as the candidate 102 responds to each of the yes/no question prompts. In some examples, speech-based auditory facets can also include any patterns of speech impediments or other type of involuntary vocalization expressed by the candidate 102 when responding to one of the yes/no baseline prompts. Other auditory facets captured by the real-time calculation engine 504 can also include sounds of breathing, coughing, or other voluntary or involuntary body movements (e.g., cracking knuckles, rubbing hands together). Additionally, the real-time calculation engine 504 can also determine the speed with which the candidate 102 replies to each of the baseline yes/no prompts.

In some examples, the backend calculation engine 506 computes a baseline state score (550) based on the mood survey data 508, which can be used in calculating baseline and response scores calculated by the real-time calculation engine 504 and the backend calculation engine 506. While FIG. 5 does not show the schematic flow for the output of baseline state score calculation (550), in some examples, the baseline state score can be used in calculating a real-time response score (532), baseline prosody score (514), baseline facial expression score (516), continuous response score (542), and overall trustworthiness and response scores (548). In some examples, the baseline state score captures an overall mood or emotional state of the candidate during the interview and can be based on detected facial expression and other mood-based features. In some embodiments, the mood-based features can include detected facial expression features and other physiological features that can indicate a level of calm/peacefulness or agitation/nervousness/anger of the candidate (e.g., respiratory rate can indicate a level of agitation or nervousness). The baseline state score can be used to normalize the other scores calculated by the system 108 based on mood indicators that are customized to both the individual and the particular interview. For example, a given candidate can have different baseline state scores in different interviews based on changes in mood of the candidate.

In some implementations, the real-time calculation engine 504 can also apply one or image processing algorithms and/or trained machine learning algorithms to detect facial expression information within the captured video data. In some implementations, the detected facial expression information can be extracted from the video data captured for the mood/emotional state (508). In some examples, the real-time calculation engine 504 can also detect changes in facial expression as the candidate 102 responds to each of the yes/no baseline prompts. For example, any changes in lip movement as the candidate 102 says "yes" or "no" (e.g., strength of a smile or frown) can be detected by the real-time calculation engine 504. In some examples, extracting the baseline facial expression features can include extracting a detected emotional expression (e.g., happiness, sadness, surprise, neutral, anger, contempt, disgust) from a subset of frames of the candidate in the baseline capture or calibration mode. Extracting baseline prosodic features (e.g., intonation, stress, rhythm of speech), in some implementations, can include extracting prosodic features from a subset of frames for each yes/no response.

In some embodiments, the auditory facet and facial expression information captured by the real-time calculation engine 504 can be used by the backend calculation engine 506 to determine at least one baseline prosody score (514) and at least one baseline facial expression score (516). The at least one baseline prosody score can include a baseline tone or inflection in the candidate's voice as the candidate 102 responds to a yes/no baseline prompt. The baseline prosody score, in some examples, can also include a baseline speed of verbal response for the candidate 102. In one example, the backend calculation engine 506 can calculate a baseline speed of verbal response for each of a "yes" and a "no" answer. Additionally, the baseline prosody scores can also include a strength of vocal tone (e.g., amplitude and frequency of the candidate's voice) for each of a "yes" and a "no" response. In some examples, the backend calculation engine 506 calculates the baseline prosody score by discarding outlier prosodic features extracted by the real-time calculation engine 504, averaging the extracted prosodic feature attributes for the remaining frames. In addition, the backend calculation engine 506 can combine and normalize subscale values for each of the prosodic features to calculate a single baseline prosody score. In one example, the baseline prosody score is a decimal value from −1 to 1 with −1 representing a negative response, 1 representing a positive response, and 0 representing a neutral response. In some examples, the calculated prosody scores can be stored in data repository 110 as baseline data 114. In some embodiments, the calculated baseline prosody scores (514) can be used by the backend calculation engine 506 in a trustworthiness score that is calculated for each of the question responses provided by the candidate 102 (518).

In some implementations, the baseline facial expression score can include a shape, size, inflection points, and/or orientation of portions of different facial features (e.g., mouth, eyes, cheeks, wrinkles, eyebrows). The baseline facial expression score can also include motion vectors characterizing the movement of each of the aspects of the detected facial features. In some examples, the motion vectors can characterize the strength, speed, and/or direction of movement of each portion and/or inflection point of a given facial feature associated with a particular response (e.g., "yes," "no," neutral) of the candidate 102. For example, for a baseline motion vector for the lips/mouth can represent how the edges of the candidate's mouth move upward as the candidate smiles when providing a "yes" response. In some examples, the backend calculation engine 506 calculates the baseline facial expression score by discarding outlier facial expression features extracted by the real-time calculation engine 504, averaging the extracted facial expression feature attributes for the remaining frames. In addition, the backend calculation engine 506 can combine and normalize subscale values for each of the facial expression features to calculate a single baseline facial expression score. In one example, the baseline facial expression score is a decimal value from −1 to 1 with −1 representing a negative response, 1 representing a positive response, and 0 representing a neutral response. In some implementations, the motion vectors, scores, and data representing the baseline facial expression can be stored in data repository 110 as baseline data 114. In some embodiments, the generated motion vectors and data representing the baseline facial expression score (516) can be used by the backend calculation engine 506 in a trustworthiness score that is calculated for each of the question responses provided by the candidate 102 (518).

In some implementations, the interview management engine 502 presents a series of interview questions to the candidate 102 via a user interface screen (520). In some examples, the interview questions can include a combination of close-ended (yes/no) and open-ended questions. In one example, the questions include a set of multiple close-ended questions followed by an open-ended question. In some examples, the questions presented to the candidate via the user interface screen are determined by the real-time calculation engine 504 (522) based on the candidate's responses to previous questions. For the first question in a series of questions presented to the candidate 102, in some implementations, the interview management engine 502 selects a question at random from a set of questions stored in data repository 110 as interview question data 112. In one example, the interview question data 112 includes multiple sets of interview questions associated with each of the candidate profiles stored as candidate profile data 118 in the data repository 110. In other examples, the interview management engine 502 may present the same first question to all candidates for a position. For example, the first question may ask the candidate 102 if he or she meets the educational requirements (e.g., bachelor's or master's degree in a particular degree field).

If a question response time limit is exceeded after presenting the interview question to the candidate 102 (524), then in some implementations, the interview management engine 502 generates an alert notifying the candidate 102 that she has not provided a timely response to the presented question (526). If the candidate 102 provides a response to the question that is detected within the predetermined time limit (528), then in some examples, the interview management engine 502 captures the response (530). In some implementations, the captured response includes video and/or audio data of the candidate's response to the question.

In some examples, the interview management engine 502 transmits the captured response data to the real-time calculation engine 504 for processing and to determine, in real time, a next question to present to the candidate 102 based on the captured response. In some implementations, the real-time calculation engine 504 calculates a response score from the captured response data based on benchmarked latency for the respective question (532). For example, each question in the interview question data 112 can have benchmarked scores associated with a candidate profile that reflects language and cultural dependencies. In some implementations, the benchmarked scores can include average or typical response speeds and/or latency for the respective question, and the calculated response score can represent an amount of difference between the captured response and the benchmarked data. For example, calculating the benchmarked speed against language-dependent norms can be calculated according to the equation, $z\_speed = ((max\_response\_time - response\_time) - average\_speed)/average\_SD$, where $z\_speed$ represents the benchmarked speed, $max\_response\_time$ represents the maximum amount of time given to the candidate to respond to the question, $average\_speed$ is the average speed for the candidate profile based on language and culturally dependent norms, and $average\_SD$ represents an average standard deviation in response times for the candidate language-cultural profile. Additionally, the real-time calculation engine 504 can perform an intra-individual norming of $z\_speeds$ for the candidate responses so that a given candidate is not disadvantaged by providing above or below-average response times. For example, the intra-individual speed ($i\_speed$) can be calculated according to the equation, $i\_speed = (z\_speed - i\_average\_speed)/i\_average\_SD$, where $i\_average\_speed$ represents the mean of the $z\_speeds$ for the candidate across all question responses, and $i\_average\_SD$ represents the standard deviation of the $z\_speeds$ for the candidate across all question responses. Further, the real-time calculation engine 504 can normalize the $i\_speed$ value for the candidate to a predetermined scale (e.g., 0 to 1). In one example, the normalized $i\_speed$ ($ni\_speed$) can be calculated according to the equation $ni\_speed = (i\_speed + 2)/4$ or $ni\_speed = (i\_speed + 3)/6$. If the calculated $ni\_speed$ is less than 0, then the $ni\_speed$ value can be set to 0. Also, if the $ni\_speed$ value is calculated to be greater than 1, then the value can be set to 1.

In some examples, the benchmarked scores for each question can be linked to the respective candidate profile data 118 in the data repository 110. In some implementations, candidate profiles can be associated with each of the job positions managed by the automated interview management system 108.

Additionally, candidate profiles can also represent different demographic profiles of potential candidates 102 that take into account cultural and language differences. For each interview question, the candidate profile can include benchmarked scores representing a base likelihood that the answer will be a "yes" or a "no" response and a benchmarked speed/latency value. The benchmarked scores can also indicate variances in strength of response in both facial expression and vocal response (prosody) based on the dominant language and/or culture of the candidate 102. For example, individuals from some cultures can on average be more expressive and vocal than other cultures. Therefore, the benchmarked scores for each of the candidate profiles can reflect these types of differences, which improves the overall accuracy of the calculations performed by the system 108. Additionally, in some implementations, the candidate profile data 118 can also be broken down into other types of candidate classifications including age, amount of education, and experience. In some implementations, the real-time calculation engine 504 can use the calculated response score for the question to update one or more of the respective candidate profile values with which the candidate 102 is associated (534). For example, the average latency, prosody, strength, and/or tone values as well as facial expression movement values for the respective candidate profiles can be updated to reflect the calculated values for the candidate 102.

In some implementations, the real-time calculation engine 504 can use the calculated response score for the respective interview question to determine a next question to present to the candidate (522). In some examples, the real-time calculation engine 504 may identify different next questions to present to the candidate 102 based on the strength and latency of the response relative to the benchmarked scores for the candidate profile. For example, if the candidate's response to a question asking whether the candidate meets minimum education requirements is slow and/or weak relative to the benchmarked scores, then in some examples, the real-time calculation engine 504 may identify a follow-up interview question also associated with the candidate's educational experience. On the other hand, if the candidate response scores for the interview question about educational experience meet and/or exceed the benchmarked values, then in some examples, the real-time calculation engine 504 may identify the next question to be one associated with a different subject, such as an amount of work experience. In some implementations, the real-time calculation engine 504 determines the next question to present to the candidate 102 based on just the response to the respective question. In other examples, the real time calculation engine 504 can determine the next question based on all of the candidate's previous scores, such as by using a cumulative score.

In some implementations, the interview question data 112 stored in data repository 110 can be organized into multiple categories based on subject matter (e.g., educational experience, work experience, work habits, personality traits). The real-time calculation engine 504, in some implementations, may select successive questions from the same question category when the calculated response score (532) for the respective question varies from the benchmarked value by more than a predetermined amount. In some examples, each category of interview question data 112 may include one or more open-ended questions that prompt the candidate 102 to provide a fulsome answer to a question that requires more than just a "yes" or a "no" response (e.g., "Explain how you responded to a difficult situation at a previous job."). The real-time calculation engine 504 may determine which open-ended question in a given category to present to the candidate 102 based on the responses to one or more of the close-ended questions in the respective category. In some aspects, the real-time calculation engine 504 may identify just one open-ended question to present to the candidate 102 after receiving responses to one or more close-ended questions in each of the question categories. In other examples, the real-time calculation engine 504 may identify an open-ended question to ask in each category after asking a series of one or more close-ended questions in the respective category. If the candidate 102 has responded to the presented open-ended question and/or if the real-time calculation engine 504 has determined that there are no more questions to present to the candidate 102 based on the candidate's previous responses (536), then in some examples, the interview management engine 502 closes the interview session.

In some examples, the real-time calculation engine 504 can also capture the direction and latency of response (538). The direction and latency of the response can include the direction of the candidate's head movement (e.g., whether the candidate answered "yes" or "no" to the question), magnitude of movement (e.g., strength of the response), and/or how long it takes the candidate 102 to provide a response. In some examples, the captured direction and latency of the response may be organized into a direction/latency feature vector that includes entries representing features associated with the response. The calculated direction and latency/speed for each question can be passed to the backend calculation engine 506 for calculating a continuous response score for the respective question (542). In one example, the continuous response score for the respective question is calculated as the direction times the normalized response speed where a "no" response is represented by a value of −1 and all other responses (e.g., "yes" and neutral) are represented by a value of 1. In some implementations, the continuous response score can represent an overall strength of the response where a strong "yes" (e.g., a candidate was quick to provide the "yes" response) is indicated by a value of 1, and a weak "yes" (e.g., a candidate was slow to provide the "yes" response) is indicated by a positive value that is close to 0. Similarly, a strong "no" (e.g., a candidate was quick to provide the "no" response) is indicated by a value of −1, and a weak "no" (e.g., a candidate was slow to provide the "no" response) is indicated by a negative value that is close to 0. In some examples, the continuous response score can be used to calculate a trustworthiness and response score for each question (518) as well as for the overall response score calculation (548).

In some examples, the real-time calculation engine 504 can also capture the prosody and facial expression of the response (540). Capturing the prosody of the response, in some implementations, can include extracting one or more prosodic features from one or more frames of the response such as voice inflection, tone, intonation, stress, rhythm, and pronunciation of the response. When extracting facial expression data from video data of the response, the real-time calculation engine 504 can extract data associated with an emotion expression of the candidate 102 while providing a response to the interview question. For example, detected features associated with emotions such as happiness, sadness, surprise, neutral, anger, contempt, disgust, and fear can be extracted. In some implementations, the system 108 can refine its detection of emotion-based features by applying the detected facial expression features along with other data (e.g., response, prosodic features) to a trained machine learning algorithm configured to identify detectable features associated with facial expressions.

The backend calculation engine 506, in some implementations, can calculate a facial expression score (544) and a reaction prosody score (546) for each response provided by a candidate 102. The facial expression score and the reaction prosody score, which can be referred to as "nonverbal" scores, can be used by the system 108 to determine whether the detected verbal response (e.g., the actual spoken "yes" or "no" response is trustworthy. In some implementations, when calculating the facial expression score (544), the backend calculation engine 506 computes a raw reaction facial expression score by discarding outlier facial expression features extracted by the real-time calculation engine 504 and averaging the extracted facial expression feature attributes for the remaining frames. In addition, the backend calculation engine 506 can combine and normalize subscale values for each of the facial expression features to calculate a single facial expression score. In one example, the facial expression score is a decimal value from −1 to 1 with −1 representing a negative response, 1 representing a positive response, and 0 representing a neutral response. In some examples, the raw facial expression score can be normalized by subtracting out the baseline facial expression score.

When calculating the prosody score, the backend calculation engine 506, in some examples, can also compute a raw prosody score by discarding outlier prosodic features extracted by the real-time calculation engine 504, averaging the extracted prosodic feature attributes for the remaining frames. In addition, the backend calculation engine 506 can combine and normalize subscale values for each of the prosodic features to calculate a single raw prosody score. In one example, the raw prosody score is a decimal value from −1 to 1 with −1 representing a negative response, 1 representing a positive response, and 0 representing a neutral response. In some examples, the raw prosody score can be normalized by subtracting out the baseline prosody score.

In some implementations, the backend calculation engine 506 can calculate a trustworthiness score for each question responded to by the candidate 102 (518). In some examples, the trustworthiness score uses quantitative representations of nonverbal aspects of the candidate response (e.g., facial expression score (544) and prosody score (546)) to determine whether the candidate's spoken response is trustworthy. For example, the trustworthiness score can provide a measure of how well the spoken response and the nonverbal aspects of the response agree with one another based on the calculated trustworthiness score. For example, if a candidate 102 provides "yes" to a question asking whether the candidate meets minimum required education requirements, but the candidate's detected facial expression is "worried" and the prosodic features indicate uncertainty (wavering tone, upward intonation when responding), then the calculated trustworthiness score may be low, indicating that the candidate's response is not trustworthy. In some examples, performing a quantitative comparison of the detected verbal to the additional detected nonverbal features of the response improves the overall accuracy of the automated reaction assessment system 108. For example, the system 108 can use the nonverbal scores to detect patterns of inconsistencies between the response provided by the candidate 102 and the nonverbal features of the responses, which can indicate that the candidate may be trying to trick the system 108 or provided a less than fully honest result. In some examples, being able to both automatically detect auxiliary, nonverbal features of a response based on detected data attributes and use those auxiliary features to determine a trustworthiness of a provided response is a technical solution to the technical problem of accurately automating the interviewing and vetting of job candidates.

In some embodiments, to calculate the trustworthiness score, the backend calculation engine 506 computes a raw nonverbal score based on the facial expression score and the prosody score, which can also be benchmarked against language-dependent norms for the candidate profile. In some examples, the raw nonverbal score (raw_nvr) can be calculated according to the equation, raw_nvr=((score_facial+score_prosody)/2)−average_raw_nvr)/sd_raw_nvr, where score_facial and score_prosody represent the facial expression score and the prosody score, respectively. Additionally, average_raw_nvr and sd_raw_nvr represent the benchmarked average and standard deviation benchmarked nonverbal scores, respectively. In some examples, the raw nonverbal score can be normalized to compute a normalized reaction score between a range between −1 and 1 by dividing the nonverbal score by 2 or 3. Also, scores less than −1 can be set to a value of −1 and scores greater than 1 can be set to a value of 1. In some examples, the normalized reaction score can be applied, along with the continuous response score for the respective question, to calculate a raw trustworthiness score (raw_trustworthiness) according to the equation, raw_trustworthiness=(continuous_response_score−non_verbal_reaction)$^2$. In addition, the raw trustworthiness score can be benchmarked against language-dependent norms for the candidate profile and/or other questions responded to by the candidate 102 and converted to a stanine-normed score according to the equation, trustworthiness-score=((raw_trustworthiness−average_trustworthiness)/sd_trustworthiness)*2+5, where average_trustworthiness and sd_trustworthiness represent benchmarked average and standard deviation trustworthiness scores, respectively. Therefore, in some examples, the trustworthiness score can be a value from 1 to 9 where 1 indicates a lowest amount of trustworthiness and 9 represents a highest amount of trustworthiness.

In some implementations, the backend calculation engine 506 can also calculate overall trustworthiness and response scores for the candidate 102 (548). In some examples, the overall trustworthiness and response scores can provide single score indicators of how well suited a candidate is for a particular job and/or how trustworthy the candidate's responses are. In one example, the overall trustworthiness score can be an average of the trustworthiness scores for all the close-ended question responses provided by the candidate 102. In some examples, if the overall trustworthiness score and/or one or more trustworthiness scores for individual questions fall below a predetermined threshold, the system 108 may reject the interview submission and/or prompt the candidate 102 to provide a new set of interview question responses. In some embodiments, the overall score for the candidate 102 can be an average of the continuous response scores for the close-ended question responses provided by the candidate 102. In some examples, the overall score for the candidate 102 provides a single score representation of the average speed with which the candidate 102 responded to the close-ended questions. The overall trustworthiness and response scores can be provided to employers 104 via one or more system-generated reports.

Although illustrated in a particular series of events, in other implementations, the steps of the automated interview process 500 may be performed in a different order. For example, updating the profile estimation (534) may be performed before, after, or simultaneously with determining the next interview question (522). Additionally, in other embodiments, the recommendation process may include more or fewer steps while remaining within the scope and spirit of the automated interview process 500.

Figure 6:
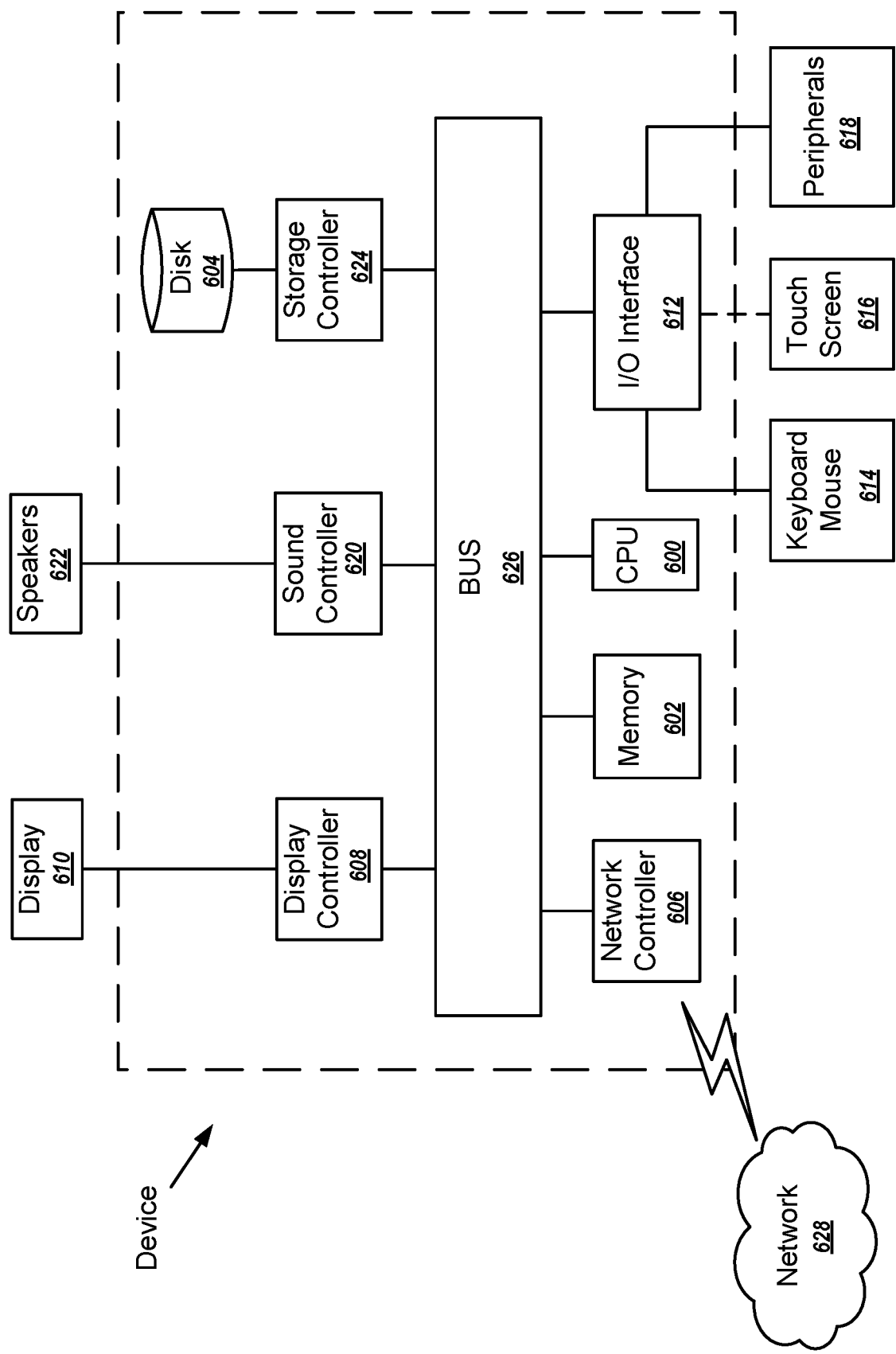
FIG. 6 is a block diagram of an example computing system.

Next, a hardware description of a computing device, mobile computing device, computing system, or server according to exemplary embodiments is described with reference to FIG. 6. The computing device, for example, may represent the candidates 102 and/or employers 104 or one or more computing systems supporting the functionality of the automated reaction assessment system 108, as illustrated in FIG. 1. In FIG. 6, the computing device, mobile computing device, or server includes a CPU 600 which performs the processes described above. The process data and instructions may be stored in memory 602. The processing circuitry and stored instructions may enable the computing device to perform, in some examples, the method 500 of FIG. 5. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device, mobile computing device, or server communicates, such as a server or computer. The storage medium disk 604, in some examples, may store the contents of the data repository 110 of FIG. 1, as well as the data maintained by the candidates 102 and/or employers 104 prior to accessing by the automated reaction assessment system 108 and transferring to the data repository 110.

Further, a portion of the claimed advancements may be provided as a utility application, background daemon, or component of an operating system, or combination thereof, executing in conjunction with CPU 600 and an operating system such as Microsoft Windows 7, 8, 10, UNIX, Solaris, LINUX, Apple MAC-OS and other systems known to those skilled in the art.

CPU 600 may be a Xeon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the inventive processes described above.

The computing device, mobile computing device, or server in FIG. 6 also includes a network controller 606, such as an Intel Ethernet PRO network interface card from Intel Corporation of America, for interfacing with network 628. As can be appreciated, the network 628 can be a public network, such as the Internet, or a private network such as an LAN or WAN network, or any combination thereof and can also include PSTN or ISDN sub-networks. The network 628 can also be wired, such as an Ethernet network, or can be wireless such as a cellular network including EDGE, 3G, 4G, and 5G wireless cellular systems. The wireless network can also be Wi-Fi, Bluetooth, or any other wireless form of communication that is known. The network 628, for example, may support communications between the automated reaction assessment system 108 and any one of the candidates 102 and/or employers 104.

The computing device, mobile computing device, or server further includes a display controller 608, such as a NVIDIA GeForce GTX or Quadro graphics adaptor from NVIDIA Corporation of America for interfacing with display 610, such as a Hewlett Packard HPL2445w LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners, such as an OfficeJet or DeskJet from Hewlett Packard. The display controller 608 and display 610 may enable presentation of user interfaces for submitting requests to the automated reaction assessment system 108.

A sound controller 620 is also provided in the computing device, mobile computing device, or server, such as Sound Blaster X-Fi Titanium from Creative, to interface with speakers/microphone 622 thereby providing sounds and/or music.

The general-purpose storage controller 624 connects the storage medium disk 604 with communication bus 626, which may be an ISA, EISA, VESA, PCI, or similar, for interconnecting all of the components of the computing device, mobile computing device, or server. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

One or more processors can be utilized to implement various functions and/or algorithms described herein, unless explicitly stated otherwise. Additionally, any functions and/or algorithms described herein, unless explicitly stated otherwise, can be performed upon one or more virtual processors, for example, on one or more physical computing systems such as a computer farm or a cloud drive.

Reference has been made to flowchart illustrations and block diagrams of methods, systems, and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Figure 7:
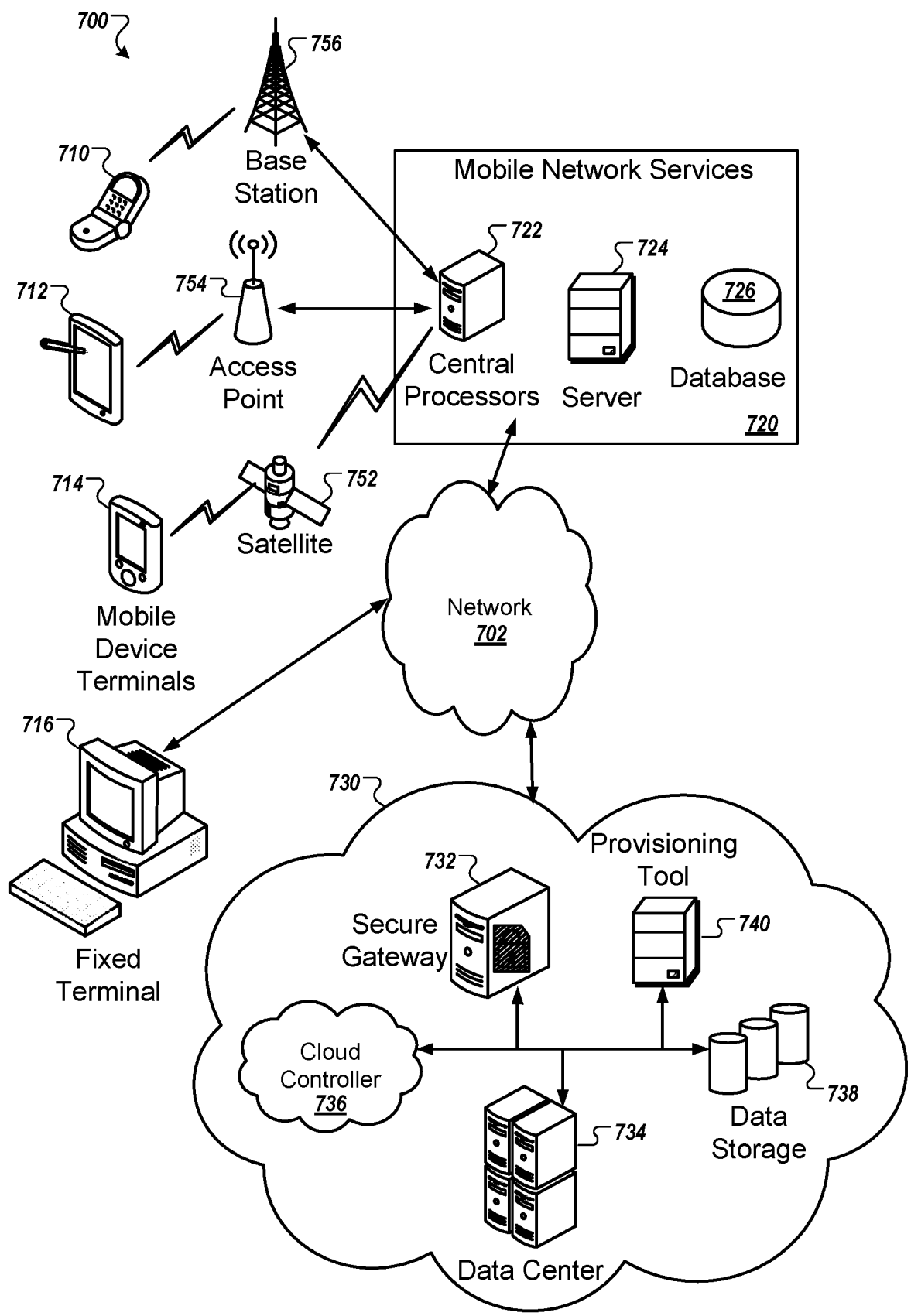
FIG. 7 is a block diagram of an example distributed computing environment including a cloud computing environment.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 7, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

In some implementations, the computing devices described herein may interface with a cloud computing environment 730, such as Google Cloud Platform™ to perform at least portions of methods or algorithms detailed above. The processes associated with the methods described herein can be executed on a computation processor, such as the Google Compute Engine by data center 734. The data center 734, for example, can also include an application processor, such as the Google App Engine, that can be used as the interface with the systems described herein to receive data and output corresponding information. The cloud computing environment 730 may also include one or more databases 738 or other data storage, such as cloud storage and a query database. In some implementations, the cloud storage database 738, such as the Google Cloud Storage, may store processed and unprocessed data supplied by systems described herein. For example, interview question data 112, baseline data 114, captured video response data 116, candidate profile data 118, question score data 120, candidate overall scores 122, training data sets 124, nonverbal response features 126, verbal response features 128, and position information 129 may be maintained by the automated reaction assessment system 108 of FIG. 1 in a database structure such as the databases 738.

The systems described herein may communicate with the cloud computing environment 730 through a secure gateway 732. In some implementations, the secure gateway 732 includes a database querying interface, such as the Google BigQuery platform. The data querying interface, for example, may support access by the automated reaction assessment system 108 to data stored on any one of the candidates 102 and/or employers 104.

The cloud computing environment 730 may include a provisioning tool 740 for resource management. The provisioning tool 740 may be connected to the computing devices of a data center 734 to facilitate the provision of computing resources of the data center 734. The provisioning tool 740 may receive a request for a computing resource via the secure gateway 732 or a cloud controller 736. The provisioning tool 740 may facilitate a connection to a particular computing device of the data center 734.

A network 702 represents one or more networks, such as the Internet, connecting the cloud environment 730 to a number of client devices such as, in some examples, a cellular telephone 710, a tablet computer 712, a mobile computing device 714, and a desktop computing device 716. The network 702 can also communicate via wireless networks using a variety of mobile network services 720 such as Wi-Fi, Bluetooth, cellular networks including EDGE, 3G, 4G, and 5G wireless cellular systems, or any other wireless form of communication that is known. In some examples, the wireless network services 720 may include central processors 722, servers 724, and databases 726. In some embodiments, the network 702 is agnostic to local interfaces and networks associated with the client devices to allow for integration of the local interfaces and networks configured to perform the processes described herein. Additionally, external devices such as the cellular telephone 710, tablet computer 712, and mobile computing device 714 may communicate with the mobile network services 720 via a base station 756, access point 754, and/or satellite 752.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A system for automatically conducting an objective evaluation of nonverbal responses made by a candidate for an available position, the system comprising:

processing circuitry; and a non-transitory computer readable memory coupled to the processing circuitry, the non-transitory computer readable memory storing machine-executable instructions, wherein the machine-executable instructions, when executed on the processing circuitry, cause the processing circuitry to receive, from a first remote computing device of a first party via a network, a video submission from the candidate for the available position, wherein
the video submission includes a plurality of baseline response video segments, determine, based on one or more nonverbal features detected within one or more of the plurality of baseline response video segments, at least one baseline nonverbal reaction score for the candidate, conduct, in real-time, an automated interview session comprising a set of interview questions selected from a plurality of close-ended interview questions, wherein each question of the plurality of close-ended interview questions is configured to elicit a response from the candidate indicating one of a respective set of potential answers, wherein the automated interview session comprises a) presenting, to the candidate via the first remote computing device, a selected interview question of the plurality of close-ended interview questions, b) receiving, from the first remote computing device responsive to the selected interview question, a question response video segment, c) identifying, from the question response video segment, a given answer of the respective set of potential answers, d) detecting candidate response attributes from the question response video segment, wherein the candidate response attributes include one or more prosodic features and/or one or more facial expression features, e) calculating, from the candidate response attributes and based on the at least one baseline nonverbal reaction score, at least one response nonverbal reaction score, and f) repeating steps a) through e) one or more times by selecting, based at least in part on the given answer and the at least one response nonverbal reaction score for a present interview question of the plurality of close-ended interview questions, a next interview question of the plurality of close-ended interview questions as the selected interview question, analyze the given answers to the set of interview questions and the response nonverbal reaction scores corresponding to the set of interview questions to identify an open-ended question of a plurality of potential open-ended questions targeted to the candidate, receive, from the first remote computing device responsive to the open-ended question, an open-ended video segment, apply at least one natural language classifier to the open-ended video segment to map a verbal portion of the open-ended video segment to a set of personality aspects, and prepare, for review by a second party, candidate interview results comprising at least one candidate score.

2. The system of claim 1, wherein at least a portion of the plurality of baseline response video segments respond to instructions to the candidate to state a word or a phrase and/or to perform a nonverbal gesture.

3. The system of claim 1, wherein the at least one baseline nonverbal reaction score comprises a baseline prosody score and a baseline facial expression score.

4. The system of claim 3, wherein calculating the at least one response nonverbal reaction score comprises:

calculating, using the baseline prosody score and the one or more prosodic features, a response prosody score for the respective interview question; and calculating, using the baseline facial expression score and the one or more facial expression features, a response facial expression score for the respective interview question.

5. The system of claim 4, wherein calculating the at least one response nonverbal reaction score comprises combining the response prosody score and the response facial expression score to generate a nonverbal reaction score for the respective interview question.

6. The system of claim 1, wherein the machine-executable instructions, when executed on the processing circuitry, cause the processing circuitry to, for each interview question of the plurality of close-ended interview questions:

detect a response direction and/or a response speed of the question response video segment for the respective interview question; and calculate, from the response direction and/or the response speed, a continuous response score reflecting a strength of a response to the respective interview question.

7. The system of claim 6, wherein the response direction is one of yes, no, or neutral.

8. The system of claim 1, wherein calculating the at least one baseline nonverbal reaction score comprises benchmarking the at least one response nonverbal reaction score against a benchmark score representative of a demographic norm corresponding to one or more of a native language or a cultural background of the candidate.

9. The system of claim 1, wherein the machine-executable instructions, when executed on the processing circuitry, cause the processing circuitry to present, to a second remote computing device of the second party responsive to receiving a request to view the candidate interview results, the candidate interview results in a graphical user interface.

10. The system of claim 1, wherein preparing the candidate interview results comprises preparing a comparison of interview results comprising the candidate interview results and interview results of at least one additional candidate to the available position.

11. A method for automatically conducting an objective evaluation of nonverbal responses made by an applicant for an available position, the method comprising:

receiving, from a first remote computing device of a first party via a network, a video submission from the applicant for the available position, wherein the video submission includes a plurality of baseline video segments;

determining, by processing circuitry based on one or more nonverbal features detected within one or more of the plurality of baseline video segments, at least one baseline nonverbal expression score for the applicant;

conducting, by the processing circuitry in real-time, an automated interview session comprising a set of interview prompts selected from a plurality of close-ended interview prompts, wherein each prompt of the plurality of close-ended interview prompts is configured to elicit a response from the applicant indicating one of a respective set of potential answers, wherein the automated interview session comprises a) presenting, to the applicant via the first remote computing device, a selected interview prompt of the plurality of close-ended interview prompts, b) receiving, from the first remote computing device responsive to the selected interview prompt, a question response video segment, c) identifying, from the question response video segment, a given answer of the respective set of potential answers, d) detecting applicant response attributes from the question response video segment, wherein the applicant response attributes include one or more prosodic features and/or one or more facial expression features, e) calculating from the applicant response attributes and based on the at least one baseline nonverbal expression score, at least one nonverbal expression score, and f) repeating steps a) through e) one or more times by selecting, based at least in part on the given answer and the at least one response nonverbal expression score for a present interview prompt of the plurality of close-ended interview prompts, a next interview prompt of the plurality of close-ended interview prompts as the selected interview prompt;

analyzing, by the processing circuitry, the given answers to the set of interview prompts and the nonverbal expression scores corresponding to the set of interview prompts to identify an open-ended prompt of a plurality of potential open-ended prompts targeted to the applicant;

receiving, by the processing circuitry from the first remote computing device responsive to the open-ended prompt, an open-ended video segment;

applying, by the processing circuitry, at least one natural language classifier to the open-ended video segment to map a verbal portion of the open-ended video segment to a set of personality aspects; and preparing, by the processing circuitry for review by a second party, applicant interview results comprising at least one applicant score.

12. The method of claim 11, wherein at least a portion of the plurality of baseline video segments were recorded responsive to instructions to the applicant to state a word or a phrase and/or to perform a nonverbal gesture.

13. The method of claim 11, wherein the at least one nonverbal expression score comprises a baseline prosody score and a baseline facial expression score.

14. The method of claim 13, wherein calculating the at least one nonverbal expression score comprises:

calculating, using the baseline prosody score and the one or more prosodic features, a response prosody score for the respective interview prompt; and calculating, using the baseline facial expression score and the one or more facial expression features, a response facial expression score for the respective interview prompt.

15. The method of claim 11, further comprising, for each interview prompt of the plurality of close-ended interview prompts:
- detecting, by the processing circuitry, a response direction and/or a response speed of the respective question response video segment for the respective interview prompt; and
- calculating, from the response direction and/or the response speed, a continuous response score reflecting a strength of a response captured in the respective question response video segment;
- wherein the response direction comprises one of yes, no, or neutral.

16. The method of claim 11, wherein calculating the at least one nonverbal expression score comprises benchmarking the at least one nonverbal expression score against a benchmark score representative of a demographic norm corresponding to one or more of a native language or a cultural background of the applicant.

17. The method of claim 11, further comprising presenting, to a second remote computing device of the second party responsive to receiving a request to view the applicant interview results, the applicant interview results in a graphical user interface.

18. The method of claim 11, wherein preparing the applicant interview results comprises preparing a comparison of interview results comprising the applicant interview results and interview results of at least one additional applicant to the available position.

* * * * *